US012702806B2

(12) United States Patent
Kim et al.

(10) Patent No.: US 12,702,806 B2
(45) Date of Patent: Aug. 11, 2026

(54) METHOD OF PROVIDING FROZEN COMPOSITION AND DEVICE THEREFOR

(71) Applicant: RECENSMEDICAL, INC., Hwaseong-si (KR)

(72) Inventors: Gun-Ho Kim, Hwaseong-si (KR); Kyongkwan Ro, Hwaseong-si (KR); Daehyun Kim, Hwaseong-si (KR)

(73) Assignee: RecensMedical, Inc., Hwaseong-si (KR)

( * ) Notice: Subject to any disclaimer, the term of this patent is extended or adjusted under 35 U.S.C. 154(b) by 0 days.

(21) Appl. No.: 19/076,259

(22) Filed: Mar. 11, 2025

(65) Prior Publication Data

US 2025/0256079 A1 Aug. 14, 2025

Related U.S. Application Data

(63) Continuation of application No. PCT/KR2024/005644, filed on Apr. 25, 2024.

(30) Foreign Application Priority Data

Apr. 25, 2023 (KR) ........................ 10-2023-0053940

(51) Int. Cl.
*A61M 35/00* (2006.01)
*A61F 7/00* (2006.01)
(Continued)

(52) U.S. Cl.
CPC ......... *A61M 35/003* (2013.01); *A61F 7/0085* (2013.01); *A61M 11/006* (2014.02);
(Continued)

(58) Field of Classification Search
CPC .... A61M 35/003; A61M 11/006; A61M 5/44; A61M 11/00; A61M 2202/03;
(Continued)

(56) References Cited

U.S. PATENT DOCUMENTS 5,219,746 A 6/1993 Brinegar et al.
6,053,889 A 4/2000 Heinzen et al.
(Continued)

FOREIGN PATENT DOCUMENTS

CN 1913977 A 2/2007
CN 102271608 A 12/2011
(Continued)

OTHER PUBLICATIONS

International Search Report and Written Opinion, with English Translation re PCT/KR2024/005643, mailed Jul. 29, 2024.
(Continued)

*Primary Examiner* — Jessica Arble
(74) *Attorney, Agent, or Firm* — Knobbe, Martens, Olson, & Bear, LLP

(57) ABSTRACT

Proposed are a method of providing a frozen composition and a device therefor and, more specifically, to a method of spraying a composition in a frozen state to a target region and a device therefor. A composition in a liquid state may be sprayed together with a refrigerant, and the composition may be frozen into a solid state by the refrigerant having a relatively low temperature and may reach the target region. The composition in a solid state may have the effect of improving skin penetration compared to the composition in a liquid state.

13 Claims, 18 Drawing Sheets

(51) Int. Cl.
*A61M 5/44* (2006.01)
*A61M 11/00* (2006.01)

(52) U.S. Cl.
CPC ................. *A61F 2007/0052* (2013.01); *A61F 2007/0063* (2013.01); *A61M 5/44* (2013.01); *A61M 11/00* (2013.01); *A61M 2202/03* (2013.01)

(58) Field of Classification Search
CPC .. A61M 5/30; A61M 5/2053; A61M 37/0069; A61F 7/0085; A61F 2007/0052; A61F 2007/0063
See application file for complete search history.

(56) References Cited

U.S. PATENT DOCUMENTS

| | | | | |
|---|---|---|---|---|
| 6,141,985 | A | 11/2000 | Cluzeau et al. | |
| 7,455,195 | B2 | 11/2008 | Mekata | |
| 8,287,566 | B2 | 10/2012 | Leopold et al. | |
| 9,109,195 | B2 | 8/2015 | Zimmermann et al. | |
| 11,213,663 | B2 | 1/2022 | Baek et al. | |
| 2004/0102768 | A1 | 5/2004 | Cluzeau et al. | |
| 2004/0222315 | A1 | 11/2004 | Habatjou | |
| 2005/0018036 | A1 | 1/2005 | Barron et al. | |
| 2006/0157584 | A1 | 7/2006 | Nomiyama et al. | |
| 2008/0038356 | A1 | 2/2008 | Maa et al. | |
| 2008/0245895 | A1 | 10/2008 | Kumono | |
| 2010/0019062 | A1 | 1/2010 | Clarke | |
| 2010/0305505 | A1 | 12/2010 | Ducharme et al. | |
| 2011/0060195 | A1 | 3/2011 | De Noray et al. | |
| 2011/0092884 | A1 | 4/2011 | Kang | |
| 2011/0101129 | A1 | 5/2011 | Anderson et al. | |
| 2011/0137268 | A1* | 6/2011 | Thomason .......... | A61M 35/003 604/291 |
| 2011/0259974 | A1 | 10/2011 | Cooper et al. | |
| 2012/0067977 | A1 | 3/2012 | Spiegel et al. | |
| 2012/0167878 | A1 | 7/2012 | Belson et al. | |
| 2013/0175363 | A1 | 7/2013 | Dobias et al. | |
| 2014/0000297 | A1 | 1/2014 | Wieland | |
| 2014/0200511 | A1* | 7/2014 | Boyden .................. | A61K 40/00 606/213 |
| 2015/0014443 | A1 | 1/2015 | Albisetti | |
| 2018/0214644 | A1 | 8/2018 | Plan | |
| 2020/0297403 | A1 | 9/2020 | Kochavi | |
| 2021/0290430 | A1* | 9/2021 | Kim .................... | A61M 35/003 |

FOREIGN PATENT DOCUMENTS

| | | | |
|---|---|---|---|
| CN | 205095992 | U | 3/2016 |
| DE | 03108918 | A1 | 9/1982 |
| JP | 2003-088781 | A | 3/2003 |
| JP | 2004-261657 | A | 9/2004 |
| JP | 2004-321806 | A | 11/2004 |
| JP | 2004-323109 | A | 11/2004 |
| JP | 2005-074341 | A | 3/2005 |
| JP | 2005-249193 | A | 9/2005 |
| JP | 2007-319729 | A | 12/2007 |
| JP | 2010-051774 | A | 3/2010 |
| JP | 2011-502006 | A | 1/2011 |
| JP | 2011-092977 | A | 5/2011 |
| JP | 2012-510344 | A | 5/2012 |
| JP | 2013-233330 | A | 11/2013 |
| JP | 2014-039916 | A | 3/2014 |
| JP | 2014-114891 | A | 6/2014 |
| JP | 6170909 | B2 | 7/2017 |
| JP | 6938195 | B2 | 9/2021 |
| JP | 2023-011924 | A | 1/2023 |
| KR | 10-0537573 | B1 | 12/2005 |
| KR | 10-1487047 | B1 | 1/2015 |
| KR | 10-1776659 | B1 | 9/2017 |
| KR | 10-2036921 | B1 | 10/2019 |
| KR | 10-2020-0070095 | A | 6/2020 |
| KR | 10-2023-0011234 | A | 1/2023 |
| RU | 2252042 | C1 | 5/2005 |
| WO | WO 1998/10750 | A2 | 3/1998 |
| WO | WO 2002/060411 | A2 | 8/2002 |
| WO | WO 2012/144990 | A1 | 10/2012 |
| WO | WO 2013/157595 | A1 | 10/2013 |
| WO | WO 2024/225794 | A1 | 10/2024 |

OTHER PUBLICATIONS

International Search Report and Written Opinion, with English Translation, re PCT/KR2024/005644, mailed Aug. 2, 2024.

* cited by examiner (a)

(b) (c)

(a)

(b)

(c)

(a)

(b)

(a)

(b)

(a)

(b)

test group 1 test group 5

(a)

| | untreated group | first experimental group | second experimental group | third experimental group |
|---|---|---|---|---|
| penetration ability (Counts (10^5)) | 2.16 | 6.22 | 4.01 | 10.51 |

(b)

METHOD OF PROVIDING FROZEN COMPOSITION AND DEVICE THEREFOR

CROSS REFERENCE TO RELATED APPLICATION

This is a continuation application of International Patent Application No. PCT/KR2024/005644 filed Apr. 25, 2024, which claims priority to Korean Patent Application No. 10-2023-0053940, filed Apr. 25, 2023, the entire contents of each of which is incorporated herein for all purposes by this reference.

BACKGROUND

Technical Field

The present disclosure relates generally to a method of providing a frozen composition and a device therefor and, more specifically, to a method of spraying a composition in a frozen state to a target region and a device therefor.

Description of Related Technology

In delivering a composition to the skin, the degree to which the composition penetrates into the skin has a significant impact on the degree of effect produced by the composition. Accordingly, various studies have been conducted to improve the penetration ability of compositions into the skin.

SUMMARY

One aspect is to enable a composition to reach a depth below the epidermis of the skin.

Another aspect is to enable a composition to reach a depth below the stratum corneum of the skin.

Another aspect is to enable a composition to reach the dermis of the skin.

Another aspect is to freeze a composition that is a liquid state at room temperature and provide the composition to the skin in a solid state.

Another aspect is to spray a composition on the skin, in which the freeze ratio of the composition reaching the skin is equal to or greater than a predetermined value.

Another aspect is to freeze a composition into particles of equal to or smaller size than a predetermined size or smaller and provide the frozen composition to the skin.

Another aspect is to provide a frozen composition to the skin at equal to or greater a predetermined velocity.

Another aspect is to provide a composition while maintaining the skin temperature at a predetermined value or within a predetermined range.

The aspects of the present disclosure are not limited to those disclosed herein, and other aspects not mentioned will be clearly understood by those skilled in the art from the following description and the accompanying drawings.

Another aspect is a method of freezing and spraying a composition, the method comprising: preparing a mixing spray system configured to spray a refrigerant and the composition, the mixing spray system including a nozzle configured to spray the refrigerant and a composition guide arranged adjacent to the nozzle; positioning the mixing spray system at a distance from a target region, wherein an orifice of the nozzle of the mixing spray system is an outlet where the refrigerant is sprayed and the orifice is positioned towards the target region; spraying, by using the mixing spray system, the composition with the refrigerant to the target region, the nozzle forming refrigerant spray stream, the composition guide guiding the composition in a liquid state to be introduced into the refrigerant spray stream, and a part of the composition in the liquid state being frozen and reaching the target region as the composition in a solid state; wherein, at one time point during when the refrigerant and the composition are sprayed through the mixing spray system, a freeze ratio representing a ratio of the composition in the solid state compared to the composition in the liquid state in an observing region is more than or equal to 5%, wherein the observing region is defined as a region an observing distance apart from the orifice of the nozzle and having an arbitrary width, in a side view of the mixing spray system, and wherein the observing distance corresponds to a distance between the orifice of the nozzle and the target region.

Another aspect is a freeze spray system for freezing and spraying a composition, the freeze spray system comprising: a refrigerant container where a refrigerant is stored with a pressure between 10 bar and 1000 bar; a refrigerant receiving unit configured to receive the refrigerant from the refrigerant container; a nozzle having an orifice of a predetermined size and configured to spray the refrigerant, the nozzle pressurizing the refrigerant passing therethrough such that the refrigerant passing the nozzle meets an atmospheric pressure and expands so that a temperature of the refrigerant decreases; a composition container containing the composition; a composition guide fluidically connected to the composition container and configured to discharge the composition, an end of the composition guide being arranged adjacent to the nozzle such that the composition is introduced into a refrigerant stream sprayed from the nozzle; a valve disposed between the refrigerant receiving unit and the nozzle and configured to control a flow of the refrigerant from the refrigerant receiving unit to the nozzle; and a controller configured to control the valve; wherein when the refrigerant and the composition are sprayed from the freeze spray system, a freeze ratio representing a ratio of the composition in the solid state compared to the composition in the liquid state is more than or equal to 5% at one time point in an observing region, and wherein the observing region is positioned an observing distance apart from the orifice of the nozzle and has an arbitrary width.

The means for solving the problem are not limited to the aforementioned means, and solutions that are not mentioned can be clearly understood by those skilled in the art from the present specification and the accompanying drawings.

According to one embodiment, it is possible to enable the composition to reach a depth below the epidermis of the skin.

According to another embodiment, it is possible to enable the frozen composition to reach the skin surface.

According to another embodiment, it is possible to control the degree of frozen of the composition reaching the skin surface.

According to another embodiment, it is possible to increase the amount of composition penetrated into the skin compared to the amount of composition provided to the skin surface.

The effects of the present disclosure are not limited to those mentioned above, and other effects not mentioned will be clearly understood by those skilled in the art from the following description and the accompanying drawings.

DETAILED DESCRIPTION

Figure 1:
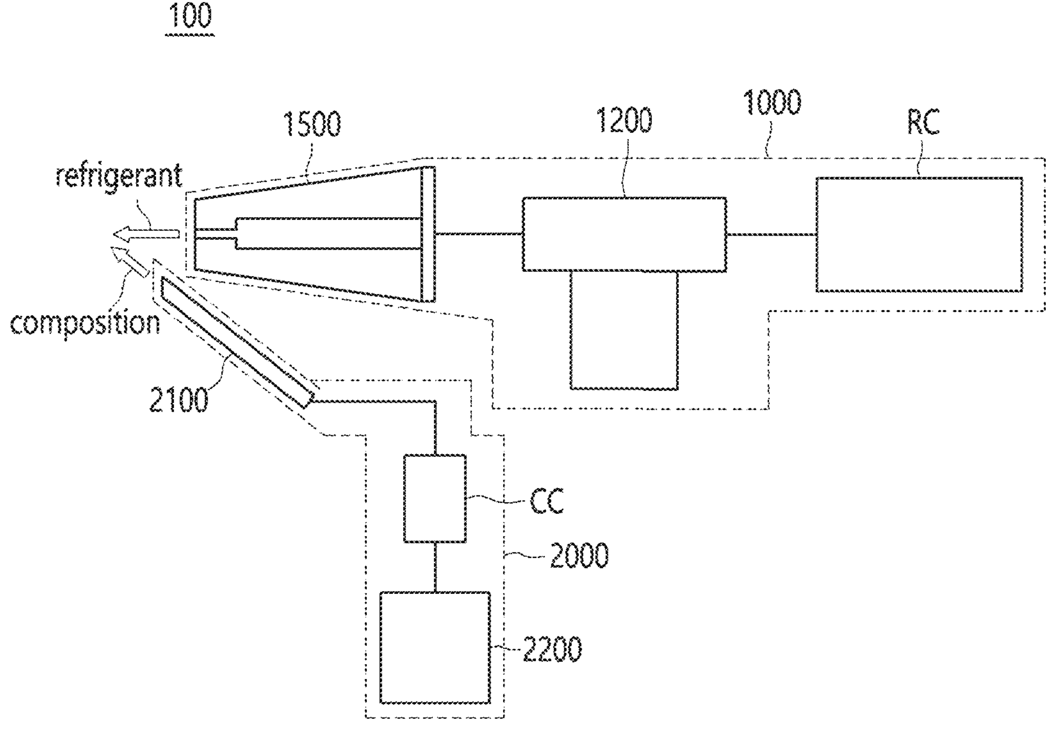
FIG. 1 is a schematic view illustrating a mixing spray system according to an embodiment.

Methods for delivering compositions to the skin include applying a composition to the skin, injecting a composition into the skin, or spraying a composition onto the skin.

Of these, it is known that the applying of the composition to the skin makes it difficult for the composition to pass through the lipid layer of the skin depending on its molecular weight and biochemical properties, and as a result, only a very small amount is absorbed into the skin.

In addition, the injecting of the composition into the skin allows the composition to penetrate deep into the skin, but inevitably damages the skin. This may cause not only pain during procedure but also problems such as bruising or swelling due to damage to the skin. Furthermore, the injecting of the composition into the skin requires operator's skill, so the penetration depth and amount may vary depending on the operator. This is disadvantageous in that the effect of the composition may be inconsistent.

Thus, there is a need for a composition delivery method that ensures the penetration ability of the composition into the skin and induces a consistent penetration effect while minimizing damage to the skin.

According to one embodiment, there provides a method of freezing and spraying a composition, the method comprising: preparing a mixing spray system configured to spray a refrigerant and the composition, the mixing spray system including a nozzle configured to spray the refrigerant and a composition guide arranged adjacent to the nozzle; positioning the mixing spray system at a distance from a target region, wherein an orifice of the nozzle of the mixing spray system is an outlet where the refrigerant is sprayed and the orifice is positioned towards the target region; spraying, by using the mixing spray system, the composition with the refrigerant to the target region, the nozzle forming refrigerant spray stream, the composition guide guiding the composition in a liquid state to be introduced into the refrigerant spray stream, and a part of the composition in the liquid state being frozen and reaching the target region as the composition in a solid state; wherein, at one time point during when the refrigerant and the composition are sprayed through the mixing spray system, a freeze ratio representing a ratio of the composition in the solid state compared to the composition in the liquid state in an observing region is more than or equal to 5%, wherein the observing region is defined as a region an observing distance apart from the orifice of the nozzle and having an arbitrary width, in a side view of the mixing spray system, and wherein the observing distance corresponds to a distance between the orifice of the nozzle and the target region.

The observing region is defined by a first line which is the observing distance apart from the orifice of the nozzle and perpendicular to a central axis of the nozzle and a second line which is the arbitrary width apart from the first line and parallel to the first line, in the side view of the mixing spray system.

The observing distance is within a recommended spray distance range determined for the mixing spray system.

The freeze ratio is, in the observing region at the one time point, a ratio of a number of particles of a composition in a solid state compared to a sum of a number of particles of a composition in a liquid state and a number of particles of a composition in a solid state.

The freeze ratio is 17% or more.

A speed of the composition in a solid state reaching the target region is 50 m/s or more.

An average size of the composition in a solid state existing in the observing region is from 20 μm to 60 μm.

According to one embodiment, there provides a freeze spray system for freezing and spraying a composition, the freeze spray system comprising: a refrigerant container where a refrigerant is stored with a pressure between 10 bar and 1000 bar; a refrigerant receiving unit configured to receive the refrigerant from the refrigerant container; a nozzle having an orifice of a predetermined size and configured to spray the refrigerant, the nozzle pressurizing the refrigerant passing therethrough such that the refrigerant passing the nozzle meets an atmospheric pressure and expands so that a temperature of the refrigerant decreases; a composition container containing the composition; a composition guide fluidically connected to the composition container and configured to discharge the composition, an end of the composition guide being arranged adjacent to the nozzle such that the composition is introduced into a refrigerant stream sprayed from the nozzle; a valve disposed between the refrigerant receiving unit and the nozzle and configured to control a flow of the refrigerant from the refrigerant receiving unit to the nozzle; and a controller configured to control the valve; wherein when the refrigerant and the composition are sprayed from the freeze spray system, a freeze ratio representing a ratio of the composition in the solid state compared to the composition in the liquid state is more than or equal to 5% at one time point in an observing region, and wherein the observing region is positioned an observing distance apart from the orifice of the nozzle and has an arbitrary width.

The observing region is defined by a first line which is the observing distance apart from the orifice of the nozzle and perpendicular to a central axis of the nozzle and a second line which is the arbitrary width apart from the first line and parallel to the first line, in the side view of the freeze spray system.

The observing distance is within a recommended spray distance range determined for the mixing spray system.

The freeze spray system further comprises a heat providing unit disposed between the refrigerant receiving unit and the nozzle and configured to heat at least part of the refrigerant moving from the refrigerant receiving unit to the nozzle; wherein the controller is, by using the heat providing unit, configured to heat the refrigerant such that the freeze ratio becomes 5% or more.

The controller is configured to apply electric power within a predetermined electric power range to the heat providing unit, wherein the heat providing unit is applied the electric power and generates a heat energy transferred to the refrigerant, and wherein the predetermined electric power range is set such that the freeze ratio becomes 5% or more.

The freeze ratio is, in the observing region at the one time point, a ratio of a number of particles of a composition in a solid state compared to a sum of a number of particles of a composition in a liquid state and a number of particles of a composition in a solid state.

The freeze spray system further comprises: an actuator coupled to the composition container and configured to supply the composition to the composition guide.

The composition guide includes an input end where the composition inflows and an output end where the composition is discharged, and wherein the output end of the composition guide is positioned within a predetermined distance from an end of the nozzle.

The above-described objectives, features, and advantages of the present disclosure will be more clearly understood from the following detailed description when taken in conjunction with the accompanying drawings. The present disclosure may, however, be embodied in many different forms and should not be limited to the exemplary embodiments. Hereinafter, reference will now be made in more detail to embodiments, specific examples of which are illustrated in the accompanying drawings.

In the drawings, the thicknesses of layers and regions are exaggerated for clarity. Further, when an element or layer is referred to as being "on" or "above" another element or layer, it can be directly above the other element or layer or intervening elements or layers may be present therebetween. In principle, like reference numerals designate like elements throughout the specification. In addition, like reference numerals are used to designate elements which have the same function within the same idea illustrated in the drawings of each embodiment, and overlapping descriptions thereof will be omitted.

Numerals (e.g., first, second, etc.) used in the description herein are merely identifiers for distinguishing one element from another element.

In addition, the element suffixes "module" and "part" used in the following embodiments are given or mixed together only considering the ease of creating the specification, and have no meanings or roles that are distinguished from each other by themselves.

As used herein, the singular forms "a", "an", and "the" are intended to include the plural forms as well, unless the context clearly indicates otherwise.

In the following embodiments, the terms "comprise", "include", "have", etc. when used in this specification, specify the presence of stated features or elements, but do not preclude the presence or addition of one or more other features or elements.

In the drawings, the sizes of elements may be exaggerated or reduced for convenience of explanation. For example, the sizes and thicknesses of elements in the drawings are arbitrarily illustrated for convenience of explanation, and embodiments of the present disclosure are not limited thereto.

When some example embodiments may be embodied otherwise, specific process steps described herein may be performed otherwise. That is, for example, two process steps described in a sequential order may be performed around the same time, or in reverse order.

In the following embodiments, when films, regions, elements, etc. are referred to as being connected to each other, they can be directly connected or be indirectly connected to each other with one or more intervening films, regions, elements, etc. interposed therebetween.

For example, when films, regions, elements, etc. are referred to as being electrically connected to each other, they can be electrically directly connected or be electrically indirectly connected to each other with one or more intervening films, regions, elements, etc. interposed therebetween.

In the following embodiments, when films, regions, elements, etc. are referred to as being fluidly connected to each other, it may be understood that they may form at least a part of a flow path through which each fluid flows.

For example, that an element A is fluidly connected to an element B may mean that a fluid passing through a flow path formed by the element A may reach a flow path formed by the element B or vice versa. Specifically, when the element A and the element B are coupled and the flow path formed by the element A and the flow path formed by the element B are directly connected to each other, the element A and the element B can be considered to be fluidly connected to each other. Otherwise, when the element A and element B are connected to each other through an element C, such as a conduit, so that the flow path formed by the element A and the flow path formed by the element B are indirectly connected to each other through a flow path formed by the element C, the element A and the element B can be considered to be fluidly connected to each other. Here, the element C can be understood as fluidly connecting the elements A and B. Furthermore, the element A and the element B may be fluidly connected to each other through a plurality of elements.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The present disclosure relates generally to a method of providing a frozen composition and a device therefor and, more specifically, to a freeze spray method of spraying a composition in a frozen state to a target region and a device therefor.

The composition may include an active substance that induces or produces a medical effect. Alternatively, the composition may include an active substance that induces or produces a cosmetic effect.

Furthermore, the composition in the present disclosure is particularly characterized by transdermal delivery, and the composition may refer to a substance that produces a cosmetic or medical effect during transdermal delivery.

The composition may include, for example, mineral, nucleic acid, amino acid, coenzyme, vitamin, niacinamide, oil-soluble licorice extract, arbutin, hyaluronic acid, potassium hyaluronate, hydrolyzed hyaluronic acid, hydrolyzed sodium hyaluronate, hydroxypropyltrimonium hyaluronate, sodium acetylated hyaluronate, sodium hyaluronate crosspolymer, sodium hyaluronate, retinol, retinyl palmitate, adenosine, peptide, coenzyme Q10, adult stem cell, antioxidant, poly-d-lactic acid (PDLA), polynucleotide, polydeoxyribonucleotide (PDRN), poly-d,l-lactic acid (PDLLA), lidocaine, botulinum toxin, exosome, proparacaine, tetracaine, human growth hormone, growth factor, cell therapy products, or a combination thereof.

Furthermore, the composition may further include: base ingredients such as purified water, glycerin, butylene glycol, propanediol, and silicone oil; ingredients that create formulations such as emulsifier, surfactant, and viscosity modifier; and preservative ingredients such as paraben, phenoxyethanol, benzoic acid, triclosan, benzyl alcohol, methylisothiazolinone, and 1,2-hexanediol.

In the present disclosure, the use of a transfer medium as a method of spraying the composition. For example, the composition may be carried by a refrigerant sprayed at a relatively high velocity and sprayed onto the target region. In this case, the temperature of the composition may be lowered by the refrigerant sprayed at a relatively low temperature.

Here, the refrigerant may be liquefied carbon dioxide ($CO_2$), carbon dioxide, liquefied nitrogen, liquefied oxygen, nitrogen dioxide ($NO_2$), nitrogen monoxide (NO), nitrous oxide ($N_2O$), hydrofluorocarbon (HFC) series materials, methane ($CH_4$), perfluorocarbon (PFC), sulfur hexafluoride ($SF_6$), or a combination thereof, and materials that can apply cooling energy to the target region, such as refrigerant and cooling gas, may be used. Meanwhile, in addition to the refrigerant, compressed air, etc. may be used.

Hereinafter, for convenience of explanation, it will be described that the composition is carried by the refrigerant and liquefied carbon dioxide is used as the refrigerant, but the technical idea of the present disclosure is not limited thereto.

Freezing a composition means that the composition in a liquid or gaseous state transitions into a solid state as the temperature thereof is lowered. The composition transitions into a solid composition with crystals when the temperature thereof is lowered. The freeze spray method to be described in the present disclosure may be understood as a method of freezing and spraying a liquid composition so that a solid composition is sprayed on the target region.

In the present disclosure, the target region refers to a region where the composition needs to be sprayed. Specifically, the target region may refer to the skin surface of a part of the human body. Alternatively, the target region may refer to the skin surface of a part of the body of an animal other than a human. The target region may be determined depending on the body part to which the composition is to be provided.

The freeze spray method described in the present disclosure has various usage examples as follows.

The freeze spray method may be used as a treatment method or medical procedure. Here, the composition refers to a drug or medicine, and may be understood to include substances used for diagnosis, curing, alleviation, treatment, or prevention of diseases or disorders, skin regeneration, lifting, and treatment of troubles such as acne and inflammation.

Doctors, etc. (medical personnel defined in each country's medical law as persons with medical expertise) may use the freeze spray method to spray a composition that has a therapeutic effect on a specific disorder or disease to persons to be treated.

The freeze spray method may be used as a cosmetic method, cosmetic procedure, or skin care. Here, the composition refers to a beauty product and may be understood to include substances that induce a cosmetic effect, such as whitening effect, skin soothing effect, nutritional supply effect, moisturizing effect, wrinkle improvement effect, or elasticity improvement effect, when applied to the skin. Furthermore, the composition may be composed of substances that have little or no effect on the human body.

Estheticians or skin care professionals may spray a composition having a cosmetic effect on persons to be treated using the freeze spray method.

The freeze spray method may be used as a treatment or cosmetic method for animals other than humans. Here, the composition refers to a drug, medicine, or beauty product, and may be understood to include an active substance that has a therapeutic or cosmetic effect.

Regarding Composition Penetration

The main purpose of the freeze spray method to be described in the present disclosure is to enable a composition to penetrate into the skin.

Meaning and Significance of Composition Penetration

Penetration of the composition means that the composition reaches a specific depth from the skin surface. More specifically, penetration of the composition means that the composition reaches a depth below the epidermis of the skin.

The epidermis is composed of stratum corneum, transparent stratum, stratum granulosum, stratum spinosum, and stratum basale. In particular, the stratum corneum functions as a skin barrier and is the main factor that hinders absorption of the composition.

Therefore, penetration of the composition means that the composition reaches at least below the stratum corneum. Since the thickness of the stratum corneum is about 10 μm to about 20 μm, penetration of the composition means that the composition reaches a depth of about equal to or greater than 0.01 mm from the skin surface.

For example, when a target to which the composition is to be provided is the face of a Korean adult, the epidermis is distributed to a depth of about 0.1 mm from the skin surface, and the dermis is distributed to a depth of about 0.1 mm to about 2 mm from the skin surface.

Penetration of the composition into the face means that from the skin surface, the composition reaches a depth of about 0.01 mm to about 2 mm, a depth of about 0.02 mm to about 2 mm, a depth of about 0.1 mm to about 2 mm, a depth of about 0.2 mm to about 2 mm, a depth of about 0.3 mm to about 2 mm, a depth of about 0.4 mm to about 2 mm, a depth of about 0.5 mm to about 2 mm, a depth of about 0.6 mm to about 2 mm, a depth of about 0.7 mm to about 2 mm, a depth of about 0.8 mm to about 2 mm, a depth of about 0.9 mm to about 2 mm, a depth of about 1 mm to about 2 mm, a depth of about 1.1 mm to about 2 mm, a depth of about 1.2 mm to about 2 mm, a depth of about 1.3 mm to about 2 mm, a depth of about 1.4 mm to about 2 mm, a depth of about 1.5 mm to about 2 mm, a depth of about 1.6 mm to about 2 mm, a depth of about 1.7 mm to about 2 mm, a depth of about 1.8 mm to about 2 mm, or a depth of about 1.9 mm to about 2 mm. Since the thickness of the epidermis and dermis may vary depending on the area in the face, a reference depth defining penetration of the composition is not limited to the above-described values.

Meanwhile, the target to which the composition is sprayed is not limited to the face, and other body parts other than the face, such as the scalp, neck, arms, legs, hands, and feet, may be the target. Here, penetration of the composition also means that the composition reaches below the stratum corneum or epidermis of each body part.

In order for the composition to achieve its purpose (e.g., inducing a therapeutic effect or cosmetic effect), it is important that it is absorbed into the skin. In order for the composition to be absorbed into the skin, the composition needs to reach and spread beyond the stratum corneum of the skin to the stratum basale or dermis. In other words, even when the composition includes an active substance with high effectiveness, the effect will inevitably be minimal when it stays in the stratum corneum of the skin.

There are three major methods of enabling the composition to penetrate into the dermis through the epidermis of the skin. They include a transcellular route, which passes directly through the stratum corneum of the epidermis, an intercellular route, which passes through the non-polar lipid layer between corneocytes, and a trans-appendageal route, which passes through appendages such as pores.

However, since the appendages occupy 0.1% of the skin surface area, the amount of penetration through the appendages is limited. Therefore, penetration through the transcellular or intercellular route is more important than the trans-appendageal route.

Conventional Composition Penetration Methods and Problems

Conventional methods for penetrating compositions into the skin include an application method of applying a composition, an injection method using a syringe, a needling method of forming holes in the skin with a microneedle after applying a composition, and a method of spraying a composition in the form of microparticles.

The application method of applying the composition to the skin surface is to enable the composition to penetrate through the transcellular or intercellular route. However, even when the applied composition passes through the stratum corneum through the transcellular route, it is blocked by the stratum granulosum of the epidermis and thus difficult to pass through the stratum spinosum or stratum basale, and as a result, it is difficult for the composition to reach the dermis. Even when the composition passes through the stratum corneum through the intercellular route, the amount of passed-through composition is very small, so the amount of the composition that reaches the dermis is not sufficient.

The injection method using the syringe is to invasively deliver the composition by inserting the syringe into the dermis or subcutaneous tissue. The injection method using the syringe is accompanied by relatively strong pain compared to other penetration methods, and is problematic in that the composition is concentratedly introduced into one point of the skin and does not spread evenly over the skin. In addition, in the case of the syringe, the position where the composition is introduced into the skin varies depending on the degree to which the syringe is inserted into the skin. Since the total thickness of the epidermis and dermis is about 2 mm, accurately inserting the syringe into the dermis is dependent on the operator's skill level, and therefore a consistent treatment effect may not be guaranteed.

The needling method involves applying the composition to the skin, forming holes in the skin using a needling device equipped with a plurality of microneedles having a micro-level length, and enabling the composition to penetrate through the holes.

In the case of the needling method, the microneedles are inserted into the skin with the composition applied thereto, or the composition penetrates into the skin through the holes formed by the microneedles. Due to the thickness of the microneedles, the holes formed in the skin are also thin, and therefore, the amount of composition that is introduced through the holes is limited.

In addition, the needling method may be accompanied by pain depending on the needle size of the needling device, and the skin is damaged as the needling device forms the holes in the skin, so additional care to restore skin damage is required after penetration of the composition. In addition, sterilization before use is essential to prevent infection caused by the needles of the needling device.

The airbrush method uses compressed air as a transfer medium and uses a fine nozzle 1500 to make the composition into relatively small microparticles and spray them on the skin. The airbrush method is a non-invasive method of providing the composition, is painless, and is easy to use. However, in the case of the airbrush method, the composition collides with the skin surface in a liquid state, making it difficult to provide an impact strong enough to physically pierce the epidermis. Consequently, in the airbrush method, the composition passes through the stratum corneum through the transcellular or intercellular route, but like the application method, it is difficult for the composition to pass through the stratum spinosum or stratum basale of the epidermis.

Composition Delivery Method Using Refrigerant

As a method of penetrating the composition into the skin, the present disclosure will describe a method using a mixing spray system 100.

FIG. 1 is a schematic view illustrating a mixing spray system 100 according to an embodiment.

The mixing spray system 100 adopts a method of spraying a composition using a refrigerant. Referring to FIG. 1, the mixing spray system 100 may include a refrigerant spray device 1000 and a composition supply device 2000.

The refrigerant spray device 1000 refers to a device that sprays the refrigerant. The refrigerant spray device 1000 includes at least a refrigerant container RC in which the refrigerant is stored, a flow regulating unit 1200 that controls movement of the refrigerant so that the refrigerant is sprayed or not sprayed from the refrigerant spray device 1000, and a nozzle 1500 through which the refrigerant is sprayed. The refrigerant spray device 1000 may further include other components required for operation in addition to those described above. Additional components of the refrigerant spray device 1000 will be described later.

The composition supply device 2000 refers to a device that provides the composition. The composition supply device 2000 may include a composition container CC that stores the composition and a composition guide 2100 that discharges the composition. The composition guide 2100 may include an input end through which the composition stored in the composition container CC is introduced, and an output end through which the composition is discharged. The composition supply device 2000 may further include other components required for operation in addition to those described above. Additional components of the composition supply device 2000 will be described later.

The composition supply device 2000 may be connected to the refrigerant spray device 1000 and provide the composition to the refrigerant sprayed from the refrigerant spray device 1000. Specifically, a refrigerant spray stream may be formed by the nozzle 1500 of the refrigerant spray device 1000, and the composition guide 2100 of the composition supply device 2000 may be disposed adjacent to the nozzle 1500.

Here, the refrigerant spray stream refers to a refrigerant flow including refrigerant particles sprayed from the nozzle 1500. The refrigerant spray stream formed by the nozzle 1500 may form a negative pressure at the output end of the composition guide 2100, and the negative pressure may enable the composition to be moved along the composition guide 2100 and introduced into the refrigerant spray stream. Alternatively, the composition supply device 2000 may include an actuator 2200 fluidly connected to the composition container CC. The composition may be supplied to the composition guide 2100 at a predetermined flow rate or a flow rate within a predetermined range by the actuator 2200 and introduced into the refrigerant spray stream.

The composition introduced into the refrigerant spray stream may collide with refrigerant particles in the refrigerant spray stream and be sprayed together. The composition in the refrigerant spray stream may be broken into small microparticles by the high velocity of the refrigerant spray stream and cooled by heat exchange with the refrigerant spray stream having a relatively low temperature. As such, the composition and the refrigerant may be mixed and sprayed in the mixing spray system 100.

Meanwhile, the internal pressure of the refrigerant container RC in which the refrigerant is stored may be about 10 bar to about 1000 bar at room temperature. Alternatively, the internal pressure of the refrigerant container RC may be about 30 bar to about 200 bar at room temperature. Alternatively, the internal pressure of the refrigerant container RC may be about 50 bar at room temperature. The internal pressure of the refrigerant container RC may be related to the velocity at which the refrigerant expands when it is discharged from the nozzle 1500 of the refrigerant spray device 1000. In other words, as the internal pressure of the refrigerant container RC increases, the velocity of refrigerant particles in the refrigerant spray stream may increase. Considering that the pressure of compressed air used in the above-described airbrush method is about 1 bar to about 5 bar, using a high-pressure refrigerant as a transfer medium can significantly increase the spray speed of the composition, thereby improving the penetration effect of the composition.

However, even after reviewing various existing literature, it was not known that the composition could effectively penetrate into the skin when the state of the composition reaching the skin surface is controlled using the mixing spray system 100. In particular, it was not known that the composition could effectively penetrate into the skin when it reached the skin surface in a "frozen" state.

There has been a history of experiments suggesting that spraying carbon dioxide and the composition together has an effect in reducing cellulite. However, this is interpreted as a cooling effect due to carbon dioxide, and does not reveal that a larger amount of composition "reached" fat cells, so it cannot provide an indicator suggesting that a relatively large amount of composition penetrated into the skin.

In the process of developing the mixing spray system 100, the present applicant conducted an experiment to determine the degree to which the composition penetrates into the skin when spraying the composition and the refrigerant together, and confirmed that the composition effectively penetrated into the skin compared to conventional methods. As a result of conducting research into the reason for this, it was confirmed that the penetration effect improved not simply because the composition was sprayed together with the refrigerant, but because the composition was sprayed in a frozen state.

More specifically, while observing the process of spraying the composition and the refrigerant together in the mixing spray system 100, the present applicant confirmed that a part of the composition that was in a liquid state before spraying was frozen by the refrigerant and collided with the skin surface in a solid state.

Figure 2:
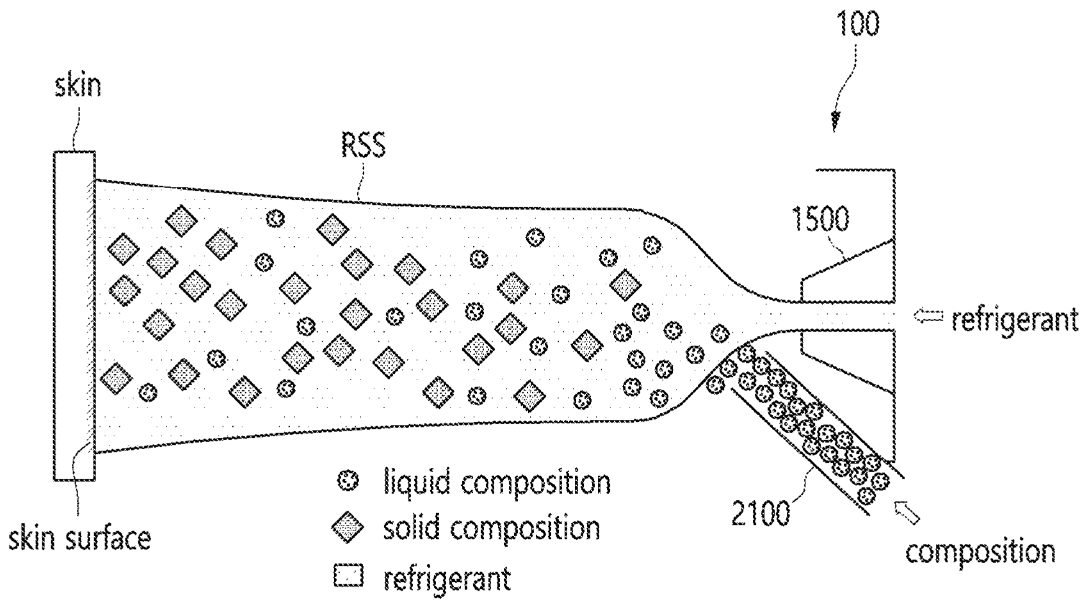
FIG. 2 is a view illustrating how a composition is frozen and sprayed according to an embodiment.

FIG. 2 is a view illustrating how the composition is frozen and sprayed according to an embodiment. Referring to FIG. 2, when a refrigerant spray stream RSS is formed by the nozzle 1500, the composition is discharged in a liquid state from the composition guide 2100 and introduced into the refrigerant spray stream RSS. As the composition in a liquid state is sprayed along the refrigerant spray stream RSS, it transitions into solid frozen particles, and the frozen particles reach the skin surface.

The present applicant assumed that the fact that the composition is frozen by the refrigerant and becomes frozen particles is a factor affecting improvement of the penetration ability of the composition, and as described later, improved the mixing spray system 100 for freeze spraying while conducting experiments on freeze spraying.

Method of Freezing and Spraying Composition

Regarding Freeze Spraying

Freeze spraying means colliding the composition in a frozen state on the skin surface so that the composition has a significant penetration effect on the skin.

The significant penetration effect means that the composition that penetrates into the skin is equal to or greater than a predetermined level. In addition, the significant penetration effect means that the composition penetrates into the skin deeply.

More specifically, the significant penetration effect means that when the composition is frozen and sprayed on the skin surface, the amount of composition reached below the epidermis of the skin is equal to or greater than a predetermined level compared to the amount of composition sprayed.

Alternatively, when the same amount of composition is mixed with the refrigerant sprayed at the same velocity and sprayed on the skin surface, the penetration effect may be significant when the amount of composition penetrated is larger than when the composition is sprayed on the skin surface in an unfrozen state.

Alternatively, the significant penetration effect means that when the composition is frozen and sprayed on the skin surface, at least a part of the composition reaches below the epidermis of the skin.

When the composition is applied to the skin surface by freeze spraying, the composition is expected to pass through the epidermis more easily. This is because when the composition is frozen and collides in the form of a solid composition with the skin surface, the impact force thereof is expected to be larger than that of a liquid composition.

Specifically, when liquid composition particles and solid composition particles with the same momentum (mass*velocity) each collide with the skin surface, the harder solid composition particles has a larger impact force due to their shorter collision time, and as a result, may more easily pass through the stratum corneum.

In addition, since the solid composition particles are crystalline solids, the collision area thereof with the skin surface may be smaller than that of the liquid composition particles. Therefore, the solid composition particles have a larger impact force per area and may pass through the stratum corneum more easily than the liquid composition particles.

The fact that the frozen composition passes through the stratum corneum may be understood that frozen particles of the composition form holes on the skin surface and penetrate into the stratum basale of the epidermis or the dermis therebelow. Since the frozen composition functions as a needle, the freeze spray method may be called an ice needling method.

Freeze Spraying with Improved Penetration Effect

As described above, freeze spraying means colliding the composition in a frozen state with the skin surface so that the composition has a significant penetration effect on the skin.

Meanwhile, the present applicant conducted an experiment on freeze spraying as described later, and confirmed that when the degree to which the composition was frozen reached a predetermined level, the penetration effect of the composition improved compared to when spraying the composition in an unfrozen state.

More specifically, it was confirmed whether penetration of the composition improved when the temperature of the refrigerant spray stream was adjusted so that the composition was moved in a frozen state until it reaches the skin surface, and as a result, it was confirmed that the penetration effect of the composition improved. A first experiment related to this will be described later.

In addition, it was necessary to confirm how the penetration effect of the composition varies depending on the degree to which the composition is frozen when it reaches the skin surface. The present applicant conducted an experiment to confirm this along with a second experiment which will be described later, and before that, established an objective criteria for the degree to which the composition was frozen in freeze spraying.

Figure 4:
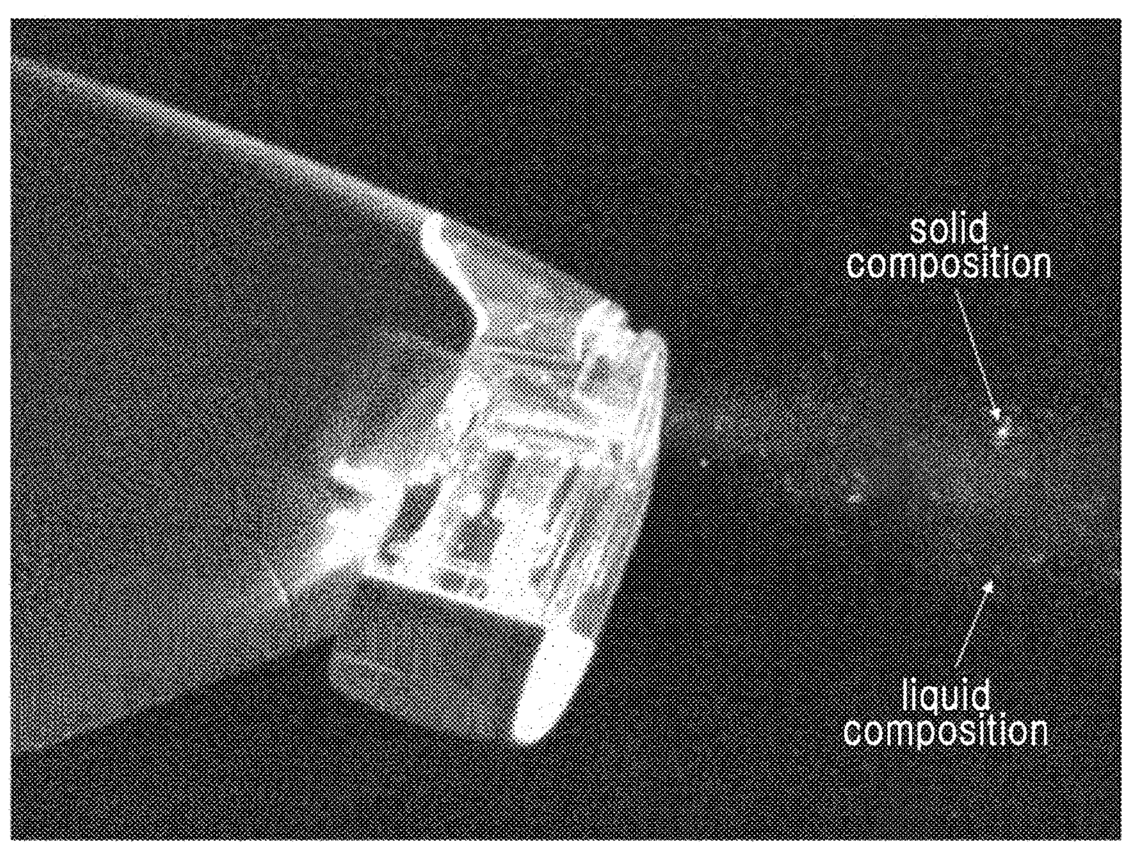
FIGS. 4 and 5 are images of a scene in which a composition in a liquid state and a composition in a solid state are sprayed according to an embodiment.

Here, as a method of determining the degree to which the composition was frozen, a method of calculating and evaluating a freeze ratio when the mixing spray system 100 is viewed from the side (e.g., the left side or right side) was used. Here, the state in which the mixing spray system 100 is viewed from the side means a state in which the mixing spray system 100 is viewed from the left or right side when operated normally. For example, the image illustrated in FIG. 4 is an image of the mixing spray system 100 when viewed from the right side. The method of calculating the freeze ratio and the method of designing the mixing spray system 100 for controlling the freeze ratio will be described later.

First, when the mixing spray system 100 performing freeze spraying is viewed from the side, and the freeze ratio is 17% (within a measurement error of 5%, about 12% to about 22%), the penetration effect is higher than when the freeze ratio is substantially 0%. Therefore, when the composition is sprayed on the skin surface with a freeze ratio of 17%, the penetration effect of the composition is significant, and spraying with the corresponding freeze ratio may be understood as freeze spraying.

In addition, when the mixing spray system 100 performing freeze spraying is viewed from the side, and the freeze ratio is 5% (within a measurement error of 1%, about 4% to about 6%), the penetration effect is higher than when the freeze ratio is substantially 0%. Therefore, when the composition is sprayed on the skin surface with a freeze ratio is 5%, the penetration effect of the composition is significant, and spraying with the corresponding freeze ratio may be understood as freeze spraying.

In addition, it was confirmed that the penetration effect of the composition improved as the freeze ratio of the composition reached the skin surface increased. Specifically, the penetration effect improved in the following order: when the freeze ratio of the composition is 5% (within a measurement error of 1%, about 4% to about 6%), when the freeze ratio of the composition is 17% (within a measurement error of 5%, about 12% to about 22%), when the freeze ratio of the composition is 48% (within a measurement error of 3%, about 45% to about 51%), when the freeze ratio of the composition is 71% (within a measurement error of 3%, about 68% to about 74%), and when the freeze ratio of the composition is 100% (within a measurement error of 1%, about 99% to about 100%).

In other words, when the penetration effect is improved under the condition that the freeze ratio of the composition is 5%, a high penetration effect can be achieved even when the freeze ratio of the composition is equal to or greater than 5%. Therefore, the freeze ratio of the composition may be adjusted from 5% to 100%. Alternatively, the freeze ratio of the composition may be adjusted from 5% to 17%. Alternatively, the freeze ratio of the composition may be adjusted from 5% to 48%. Alternatively, the freeze ratio of the composition may be adjusted from 5% to 71%.

Considering the measurement error range, the freeze ratio of the composition may be adjusted from 2% to 100%. Alternatively, the freeze ratio of the composition may be adjusted from 2% to 22%. Alternatively, the freeze ratio of the composition may be adjusted from 2% to 51%. Alternatively, the freeze ratio of the composition may be adjusted from 2% to 74%.

Meanwhile, it was confirmed that when the skin surface was excessively cooled by the refrigerant or composition in the process of increasing the freeze ratio of the composition, the penetration effect of the composition decreased. More specifically, even when the freeze ratio of the composition reaching the skin surface is high, a decrease in the temperature of the skin surface may cause a penetration-impeding substance such as an ice film to be formed, thus impeding the composition from reaching the skin surface. In this case, the penetration effect of the composition may be decreased. Therefore, it is necessary to design the mixing spray system 100 in consideration of increasing the freeze ratio of the composition while maintaining the temperature of the skin surface equal to or greater than an appropriate temperature, and the specific design method will be described later.

As in the examples above, when the mixing spray system 100 performing freeze spraying is viewed from the side, the freeze ratio is calculated, and when the penetration effect is higher than when the freeze ratio is 0%, the composition is frozen and sprayed with a freeze ratio equal to or greater than the calculated freeze ratio. This may be understood as freeze spraying.

Hereinafter, the method of calculating the freeze ratio will be described with reference to FIGS. 3 to 6.

Figure 3:
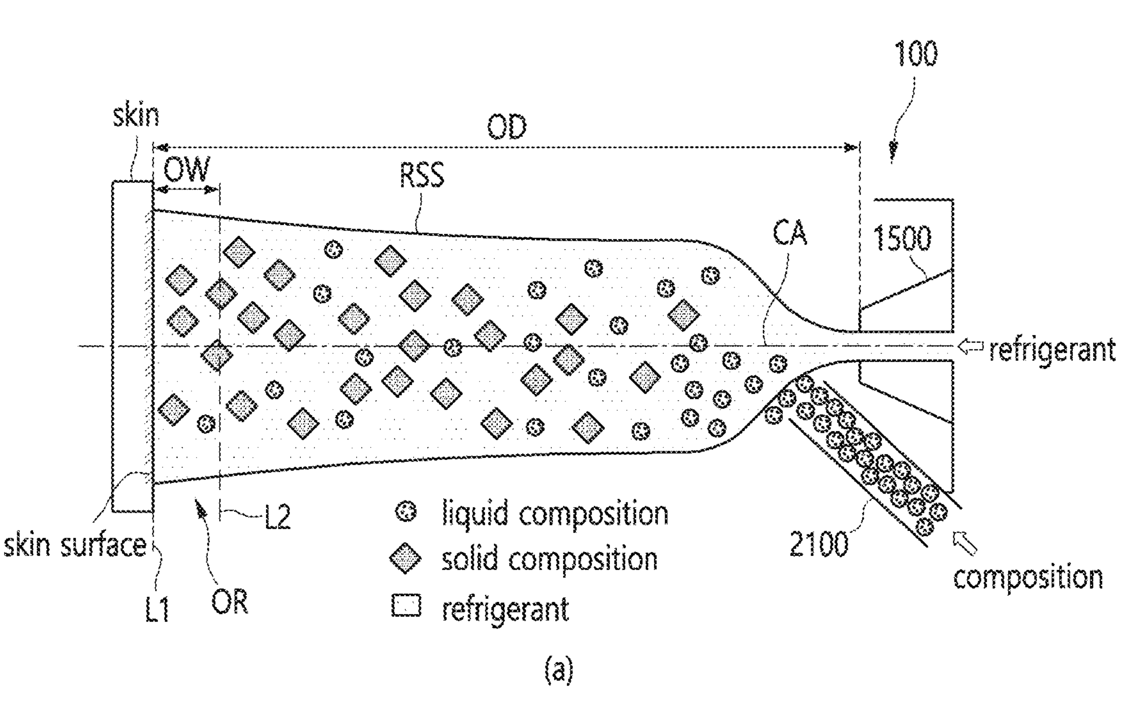
FIG. 3 is a view illustrating how the freeze ratio of the composition is determined using an observing region according to an embodiment.
Figure 3:
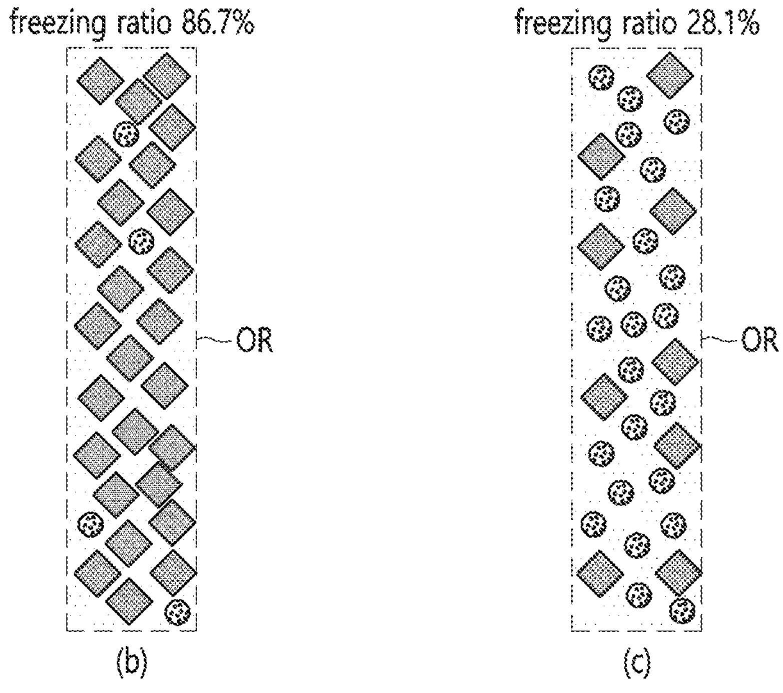

FIG. 3 is a view illustrating how the freeze ratio of the composition is determined using an observing region OR according to an embodiment. (a) of FIG. 3 illustrates that the observing region OR is specified based on the mixing spray system 100, and (b) of FIG. 3 and (c) of FIG. 3 respectively illustrate cases with different freeze ratios in the observing region OR.

Calculation of Freeze Ratio of Composition in Observing Region

A high-speed camera may be used as a means of observing freeze spraying. Specifically, when the mixing spray system 100 sprays the refrigerant and the composition, the refrigerant spray stream RSS into which the composition introduced may be captured using the high-speed camera. An image or video captured with the high-speed camera clearly shows the form in which the composition is sprayed at a time point or over a time period, and the degree to which the composition is frozen may be determined through the image or video.

The observing region OR may be specified to observe freeze spraying. The observing region OR may refer to a region for determining the freeze ratio.

Specifying the observing region OR is to determine the freeze ratio of the composition reaching the skin surface. As the composition is sprayed together with the refrigerant, the composition may be frozen in any region within the refrigerant spray stream RSS. However, since freeze spraying is aimed at penetrating the composition into the skin, it is desirable to determine whether the composition that actually reaches the skin surface is frozen or determine at which ratio the composition is frozen. In other words, considering that the purpose of freeze spraying is to determine the freeze ratio that affects the penetration effect of the composition, it is desirable to observe a region adjacent to the skin surface during freeze spraying rather than observing the entire region where the composition can be frozen.

The observing region OR may be specified based on a position corresponding to the skin surface where the composition needs to be sprayed. For example, referring to (a) of FIG. 3, when the composition is sprayed on the skin surface by the above-described mixing spray system 100, a region spaced apart from an orifice of the nozzle 1500 of the mixing spray system 100 by a distance corresponding to a separation distance between the orifice of the nozzle 1500 and the skin surface when the mixing spray system 100 is viewed from the side may be specified as the observing region OR.

More specifically, when the mixing spray system 100 is viewed from the left or right side, a virtual first straight line L1 that is spaced apart from the orifice of the nozzle 1500 of the mixing spray system 100 by an observing distance OD and is orthogonal to a central axis CA of the nozzle 1500 may be determined. In addition, when the mixing spray system 100 is viewed from the left or right side, a second straight line L2 that is parallel to the first straight line L1 and is spaced apart from the first straight line L1 by an observing width OW in a direction toward the nozzle 1500 (or in a direction away from the nozzle 1500) may be determined. The observing region OR may be determined as a region between the first straight line L1 and the second straight line L2.

The observing distance OD may be determined based on a recommended spray distance. Alternatively, the observing distance OD may be determined based on an end of a distance maintenance unit, which will be described later. Alternatively, the observing distance OD may be determined based on the length of the distance maintenance unit.

Here, the recommended spray distance may refer to a distance at which the mixing spray system 100 needs to be positioned relative to the skin surface in the use of the mixing spray system 100. Specifically, the recommended spray distance may refer to a preferred straight-line distance between the nozzle 1500 and the skin surface when operating the mixing spray system 100 to spray the refrigerant and the composition on the skin surface. The recommended spray distance may be determined differently depending on the specifications of the components of the mixing spray system 100 (e.g., the internal pressure of the refrigerant container RC, the size of the orifice of the nozzle 1500, etc.).

The recommended spray distance is preferably longer than the length of an acceleration section required for the composition to accelerate. Specifically, the composition is frozen after being introduced into the refrigerant spray stream RSS, and the frozen composition is accelerated over a predetermined section. In order for frozen particles of the composition to be sufficiently accelerated, an acceleration section having a predetermined length in a direction parallel to the central axis CA of the nozzle 1500 is required. For example, in order for frozen particles of the composition to be sufficiently accelerated, an acceleration section of about 3 mm to about 5 mm or about 1 mm to about 10 mm is required. It is preferable that the above-described acceleration section is guaranteed based on a position where the composition is introduced into the refrigerant spray stream RSS. Therefore, the recommended spray distance may be set to be greater than the sum of the distance from the orifice of the nozzle 1500 to the position where the composition is introduced into the refrigerant spray stream RSS and the length of the above-described acceleration section based on the direction parallel to the central axis CA of the nozzle 1500.

The recommended spray distance is preferably longer than the length of the acceleration section required for the composition to accelerate.

In addition, the recommended spray distance is preferably longer than the length of a freeze section required for the composition to be introduced into the refrigerant spray stream RSS and frozen.

The recommended spray distance may be selected within a range of, for example, 3 mm to 100 mm. Meanwhile, since the recommended spray distance is a guide to the preferred spray distance, it may be presented as a range rather than a specific value. For example, the recommended spray distance may be presented as a range having a lower distance limit value and an upper distance limit value selected within a range of 3 mm to 100 mm.

The observing distance OD may be the same as the recommended spray distance. When the observing distance OD is the same as the recommended spray distance, a region where the skin surface is expected to be located may be specified as the observing region OR.

Meanwhile, the observing distance OD may be shorter than the recommended spray distance. When, the process of spraying the composition and the refrigerant on the skin surface is captured with the high-speed camera, it is difficult to determine the freeze ratio of the composition on the skin surface. Therefore, the freeze ratio determined at a predetermined distance from the skin surface may be estimated as the freeze ratio on the skin surface. In this case, the observing distance OD may be shorter than the recommended spray distance. Alternatively, when the mixing spray system 100 is viewed from the side, the observing region R may be determined by the first straight line L1 spaced from the skin surface by a first distance and the second straight line L2 parallel to the first straight line L1 and spaced apart from the first straight line L1 by the observing width OW.

The observing distance OD may be set to be greater than the recommended spray distance. In this case as well, the freeze ratio in the observing region OR may be estimated as the freeze ratio on the skin surface.

When the recommended spray distance is presented as a range, the observing distance OD may be included within the recommended spray distance range. The recommended spray distance range may be determined as a section within a range of 3 mm to 100 mm.

Meanwhile, the observing distance OD does not necessarily need to be determined based on the recommended spray distance, and may be determined arbitrarily.

The observing distance OD may be set to be greater than a minimum threshold distance value. In order for the composition to be introduced into the refrigerant spray stream RSS and frozen, heat exchange needs to occur between the refrigerant and the composition, so heat exchange takes a predetermined amount of time. Since the composition is moved by the refrigerant during heat exchange, the composition may not be frozen in a region closest to the nozzle 1500 through which the refrigerant is sprayed. Therefore, considering that the observing region OR is set to observe frozen particles, the observing distance OD may be set to be greater than the distance corresponding to the closest region from the nozzle 1500. For example, the observing distance OD may be set to be greater than a minimum threshold distance value determined within a range of 0 mm to 3 mm.

The observing width OW refers to a width of the observing region OR.

The observing width OW may be determined within a range of 1% to 50% of the observing distance OD. Alternatively, the observing width OW may be determined as the diameter of the refrigerant spray stream RSS at a position spaced apart by the observing distance OD from the orifice of the nozzle 1500. Alternatively, the observing width OW may be determined as an average diameter of the refrigerant spray stream RSS. Meanwhile, the observing width OW may not be specified as an arbitrary value, and the inside of the refrigerant spray stream RSS that can be seen with the naked eye may be the observing region OR.

The freeze ratio may be defined as a ratio of the number of solid composition particles to the sum of the number of solid composition particles and the number of liquid composition particles in a specific region. For example, referring to (b) of FIG. 3 or (c) of FIG. 3, the freeze ratio may be obtained by counting the number of solid composition particles and the number of liquid composition particles observed in the observing region OR and dividing the number of solid composition particles by the sum of the number of solid composition particles and the number of liquid composition particles.

Meanwhile, the freeze ratio may further take into account the number of gas composition particles. However, since it is difficult to calculate the number of gas composition particles, and the composition mostly exists in a solid or liquid state when the refrigerant and the composition are sprayed together, it is preferable that the freeze ratio does not take into account the number of gas composition particles.

Hereinafter, a method of identifying solid composition particles in captured images will be described with reference to FIGS. 4 to 6.

Figure 5:
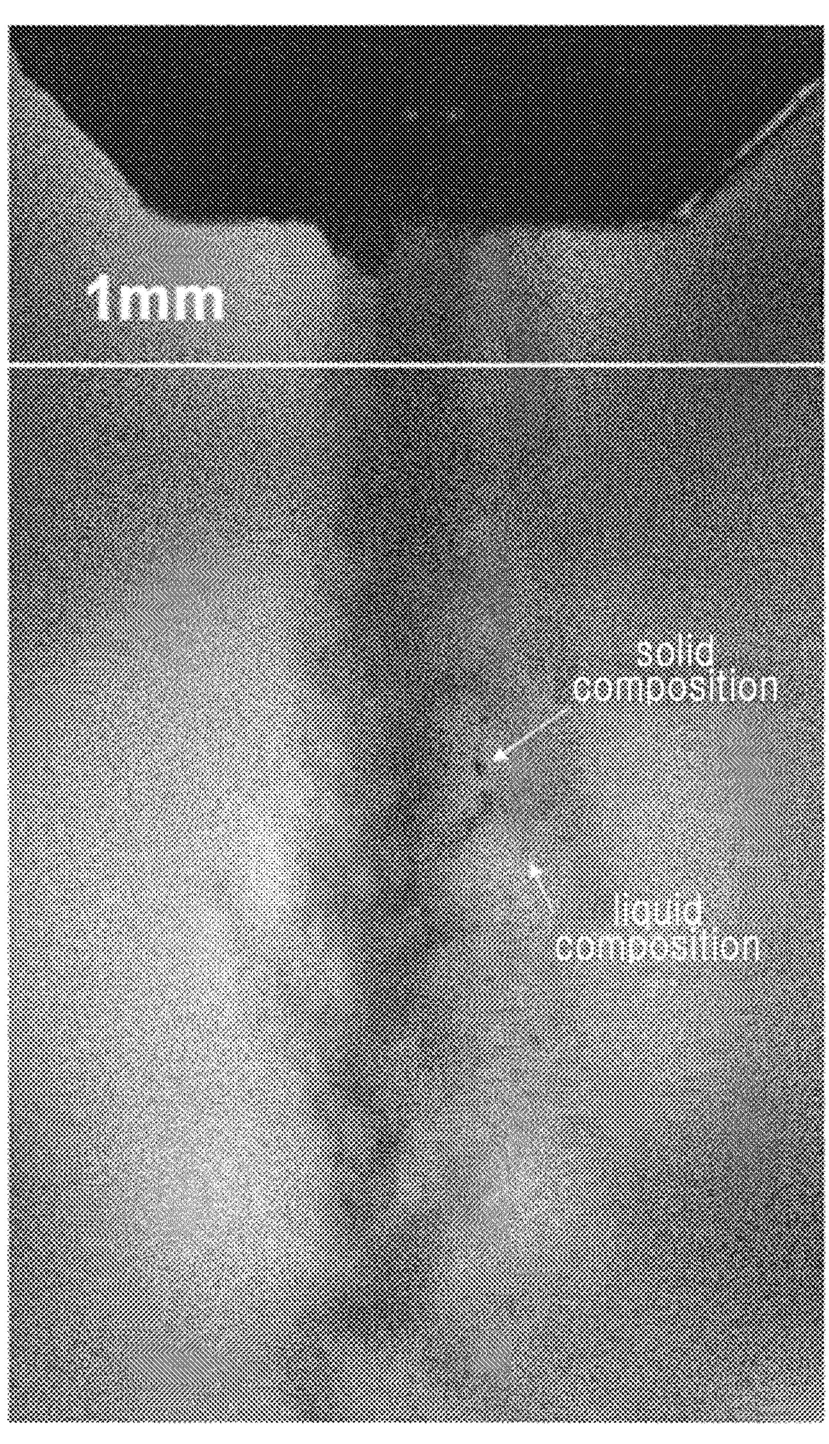

FIGS. 4 and 5 are images of a scene in which the liquid composition and the solid composition are sprayed according to an embodiment. FIG. 4 illustrates an image captured with the high-speed camera while light is emitted toward the mixing spaying system 100 that sprays the composition and the refrigerant. FIG. 5 illustrates an image of the mixing spray system 100 that sprays the composition and the refrigerant captured with the high-speed camera, in which light is emitted toward the high-speed camera and blocked by the composition.

Figure 6:
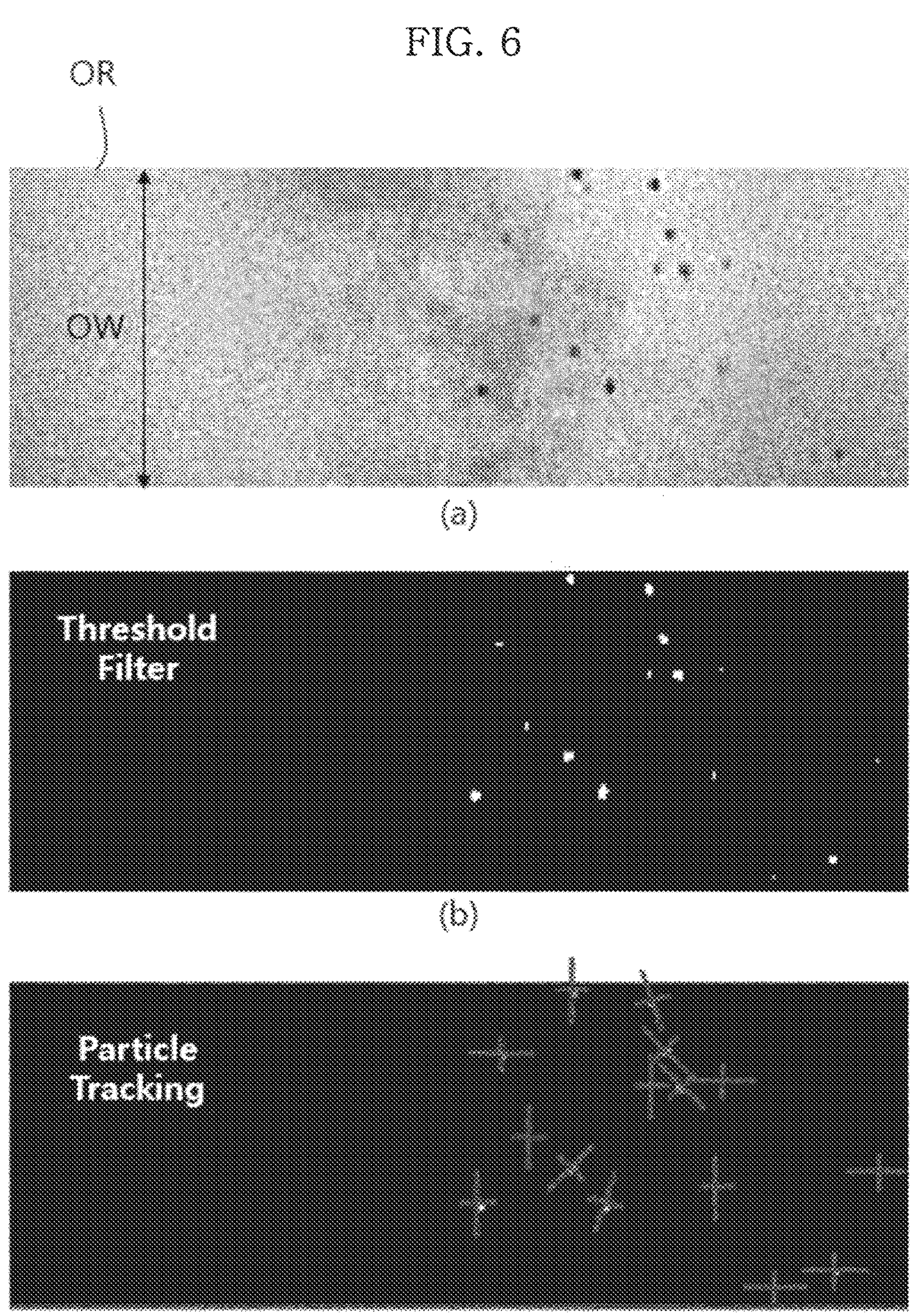
FIG. 6 is a view illustrating an image processing process for counting solid composition particles according to an embodiment.

FIG. 6 is a view illustrating an image processing process for counting solid composition particles according to an embodiment. (a) of FIG. 6 illustrates an image of the observing region OR, (b) of FIG. 6 illustrates an image obtained by applying a threshold filter to the image of (a) of FIG. 6, and (c) of FIG. 6 illustrates tracking solid composition particles in the image of (b) of FIG. 6.

In calculating the freeze ratio, solid composition particles and liquid composition particles may be visually distinguished in high-speed camera images or videos (hereinafter referred to as "images, etc."). Specifically, referring to FIG. 4, since the solid composition particles have a crystalline form, they reflect light and appear relatively bright.

Therefore, among the particles visibly identified in the images, etc. captured with the high-speed camera, particles that reflect light and appear bright may be specified as the solid composition particles, and particles that do not reflect light and appear dark may be specified as the liquid composition particles.

In addition, as illustrated in FIG. 5, the liquid composition particles and the solid composition particles may be distinguished based on the brightness of composition particles in images, etc. captured with the high-speed camera. Referring to FIG. 5, since the solid composition particles are darker than the liquid composition particles, the solid composition particles and the liquid composition particles may be identified based on the brightness with a predetermined level.

Referring to FIG. 6, the solid composition particles may be counted by separating the observing region OR from images, etc. captured with the high-speed camera, applying a filter that selects pixels with a brightness equal to or less than a predetermined level of brightness to the observing region OR, and tracking pixels that occupy more than a predetermined region.

In addition to the above-described methods for identifying solid composition particles, dynamic light scattering (DLS) with polarization analysis, time-resolved X-ray diffraction (TR-XRD), or in situ spectroscopy may be used.

Meanwhile, the freeze ratio may be defined as a ratio of the area of the solid composition particles to the sum of the area of the solid composition particles and the area of the liquid composition particles in a specified region.

According to an embodiment, the freeze ratio may be calculated in the following manner.

First, an image may be acquired using the high-speed camera while the composition and the refrigerant are sprayed together by the mixing spray system 100. Then, the observing region OR may be specified in the acquired image, and the freeze ratio may be calculated in the specified observing region OR.

Here, a plurality of images may be acquired.

For example, freeze spraying may be performed n times (n is a natural number of equal to or greater than 2) by the mixing spray system 100, and in an nth trial freeze spraying process, an nth trial image captured at a preset time after the start of spraying may be acquired. Thereafter, an nth trial freeze ratio may be calculated from the nth trial image, and the average of the first freeze ratio to the nth trial freeze ratio may be obtained as a final freeze ratio. Here, performing freeze spraying n times may be understood that spraying the composition and the refrigerant is performed n times in a state in which the same amount of refrigerant is stored at the same pressure in the refrigerant container RC and the same amount of composition is stored in the composition container CC.

For another example, the refrigerant and the composition may be sprayed from the mixing spray system 100 during a preset capture time, and at least two or more images may be acquired among images acquired during the capture time. The observing region OR may be specified and the freeze ratio may be calculated from each captured image, and the average of each freeze ratio for each captured image may be obtained as a final freeze ratio.

Meanwhile, when the plurality of images are acquired, in addition to averaging each freeze ratio obtained in each image, the freeze ratio may be calculated by adding the number of solid composition particles and the number of liquid composition particles counted in each image.

As described below, the penetration effect of the composition may vary depending on the freeze ratio. For example, as the freeze ratio increases, the penetration effect of the composition may increase.

Therefore, the mixing spray system 100 needs to be designed so that a freeze ratio at which a significant composition penetration effect is achieved is found and freeze spraying is performed with the corresponding freeze ratio.

In the above, it has been described that calculation of the freeze ratio in the observing region OR is understood as freeze spraying, but the technical idea of the present disclosure is not limited thereto.

For example, when the number of frozen particles in the observing region OR is equal to or greater than a preset threshold particle number when the composition and the refrigerant are sprayed together, this may be understood as freeze spraying.

Here, the threshold particle number is a value when the composition penetration effect on the skin is higher than when the number of frozen particles is substantially 0, and may be specified through experiments.

Meanwhile, a method of counting the number of frozen particles in the observing region OR is the same as the method of counting the number of frozen particles of the composition among the above-described freeze ratio calculation methods.

In the above, the method of specifying the observing region OR and calculating the freeze ratio when the mixing spray system 100 or spraying the composition and the refrigerant are viewed from the side has been described. However, the technical idea of the present disclosure is not limited thereto, and it is also possible to specify the observing region OR and calculate the freeze ratio when the mixing spray system 100 or spraying the composition and the refrigerant are viewed from above or below. Furthermore, it is also possible to calculate the freeze ratio by counting the solid composition particles and the liquid composition particles when viewing from two or more directions.

Likewise, when viewing from a direction other than the side or from two or more directions, a freeze ratio with a significant penetration effect may be calculated through experiments, and spraying the composition and the refrigerant with a freeze ratio equal to or greater than the corresponding freeze ratio may be understood as freeze spraying.

Calculation of Freeze Ratio of Composition Passing Through Observing Line

The freeze ratio may be calculated based on an observing line OL as described below.

Figure 7:
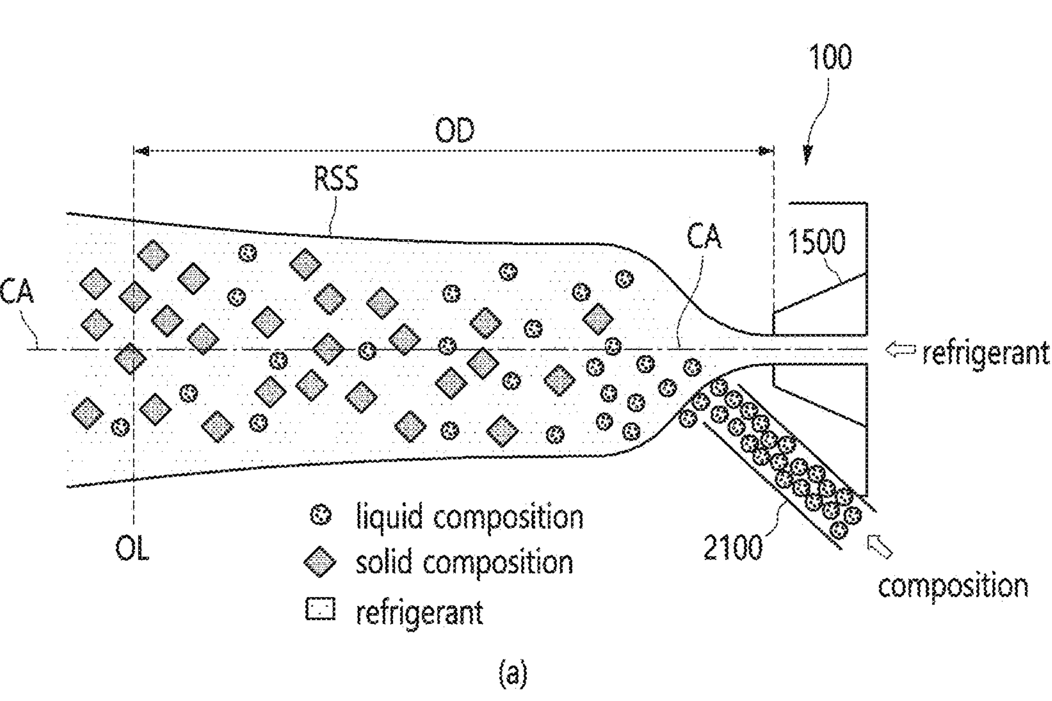
FIG. 7 is a view illustrating how the freeze ratio is calculated using an observing line according to an embodiment.
Figure 7:
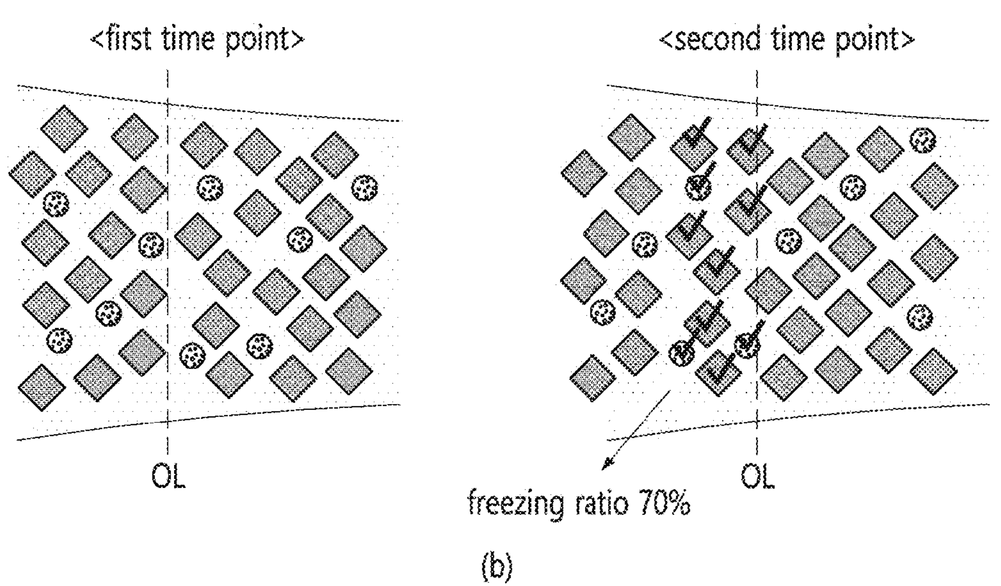

FIG. 7 is a view illustrating how the freeze ratio is calculated using the observing line OL according to an embodiment. (a) of FIG. 7 illustrates that the observing line OL is specified based on the mixing spray system 100, and (b) of FIG. 7 illustrates composition particles that passed through the observing line OL at first and second time points.

The observing line OL may be specified based on a position corresponding to the skin surface where the composition needs to be sprayed. For example, referring to (a) of FIG. 6, when the mixing spray system 100 that sprays the composition is viewed from the side, a straight line spaced a predetermined distance apart from the mixing spray system 100 may be specified as the observing line OL. More specifically, when the mixing spray system 100 is viewed from the left or right side, a virtual straight line that is spaced apart from the orifice of the nozzle 1500 of the mixing spray system 100 by an observing distance OD and is orthogonal to the central axis CA of the nozzle 1500 may be determined as the observing line OL.

Here, the observing distance OD is the same as that described in the observing region OR.

The freeze ratio may be calculated as a ratio of the number of frozen particles of the composition to the sum of the number of solid composition particles and the number of liquid composition particles passing through the observing line OL over a predetermined period of time. More specifically, referring to (b) of FIG. 7, the freeze ratio may be calculated in the following manner. First, an image may be acquired by capturing the side of the mixing spray system 100 that sprays the composition using the high-speed camera. Then, in the image, an image frame corresponding to a random first time point and an image frame corresponding to a second time point may be selected. Finally, in the selected image frames, the number of liquid composition particles and the number of solid composition particles that passed through the observing line OL from the first time point to the second time point may be counted.

The freeze ratio may be obtained as an average value of individual freeze ratios obtained for a plurality of images. Here, the plurality of images may include images obtained from each nth trial freeze spraying process. Also, here, the plurality of images may refer to images acquired in n time periods among images obtained by capturing spraying of the composition and the refrigerant from the mixing spray system 100 for a predetermined period of time.

As described in the observing region OR, the method of calculating the freeze ratio using the observing line OL may also assume that the mixing spray system 100 is viewed from above, below, or from two or more directions as well as from the side.

Calculation of Freeze Ratio of Composition Sprayed on Observing Surface

The freeze ratio may be calculated using an observing surface as described below.

First, the observing surface may be placed at a position spaced apart by the observing distance OD in the mixing spray system 100, and the composition and the refrigerant may be sprayed on the observing surface while the high-speed camera captures the observing surface.

Thereafter, an image frame corresponding to a time point when the composition first reaches the observing surface or a time point after a predetermined period of time therefrom may be acquired from images captured by the high-speed camera.

The solid composition and the liquid composition may be distinguished based on color differences (or brightness differences) on the observing surface of the acquired image frame, and therefore, the area occupied by the solid composition and the area occupied by the liquid composition may be calculated based on the observing surface.

The freeze ratio may be calculated as a ratio of the area occupied by the solid composition to the sum of the area occupied by the solid composition and the area occupied by the liquid composition.

In the method of calculating the freeze ratio using the observing surface, a sensor that distinguishes between liquid and solid may be used in addition to the high-speed camera. For example, changes in temperature of an insulated plate may be monitored while spraying the composition and the refrigerant on the insulated plate, and the freeze ratio may be calculated based on the changes in temperature of the insulated plate or the amount of cooling energy (or heat) required to maintain the temperature and the latent heat absorbed by frozen particles when they transition into liquid. For another example, an electric touch sensor may be installed on the observing surface, and considering the capacitance upon contact of the liquid composition and the solid composition to the observing surface, the freeze ratio may be estimated based on the change in measured electrical signals.

In the method of calculating the freeze ratio using the observing surface, using the electric touch sensor Method of Generating Frozen Particles Hereinafter, a method for generating frozen particles by freezing the composition will be described with reference to FIGS. 8 to 11.

As described above, frozen particles of the composition may be generated using the mixing spray system 100. Specifically, the refrigerant spray stream RSS having a relatively low temperature may be formed by the refrigerant spray device 1000 of the mixing spray system 100, and frozen particles may be generated while the composition is supplied to the refrigerant spray stream RSS by the composition supply device 2000 of the mixing spray system 100.

Figure 8:
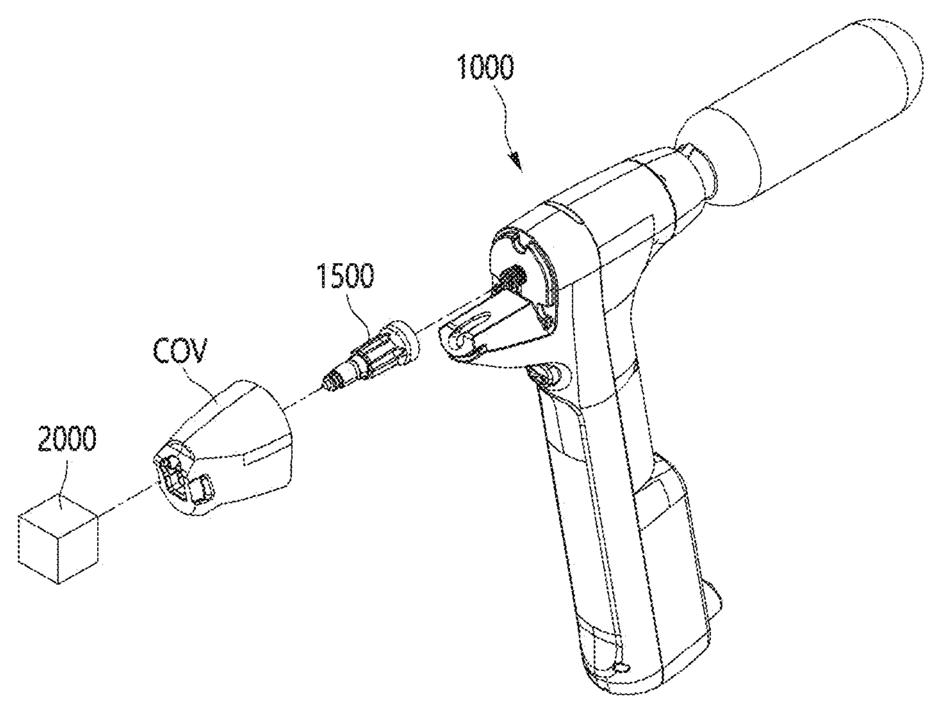
FIG. 8 is a view illustrating a mixing spray system according to an embodiment.

FIG. 8 is a view illustrating a mixing spray system 100 according to an embodiment. Referring to FIG. 8, the mixing spray system 100 may include a refrigerant spray device 1000 and a composition supply device 2000. The composition supply device 2000 may be coupled to a nozzle 1500 of the refrigerant spray device 1000.

Meanwhile, as illustrated in FIG. 8, the mixing spray system 100 may further include a cover COV that covers the nozzle 1500 and supports the composition supply device 2000.

Hereinafter, for convenience of explanation, it will be described that the composition supply device 2000 is coupled to the nozzle 1500 of the refrigerant spray device 1000, but the technical idea of the present disclosure is not limited thereto. In addition to the nozzle 1500, the composition supply device 2000 may be coupled to the cover COV or a housing of the refrigerant spray device 1000. However, even in this case, a composition guide 2100 of the composition supply device 2000 needs to be disposed adjacent to the nozzle 1500 of the refrigerant spray device 1000 so that a composition discharged from the composition guide 2100 is introduced into a refrigerant spray stream RSS formed at the nozzle 1500.

Detailed Component of Mixing Spray System

Figure 9:
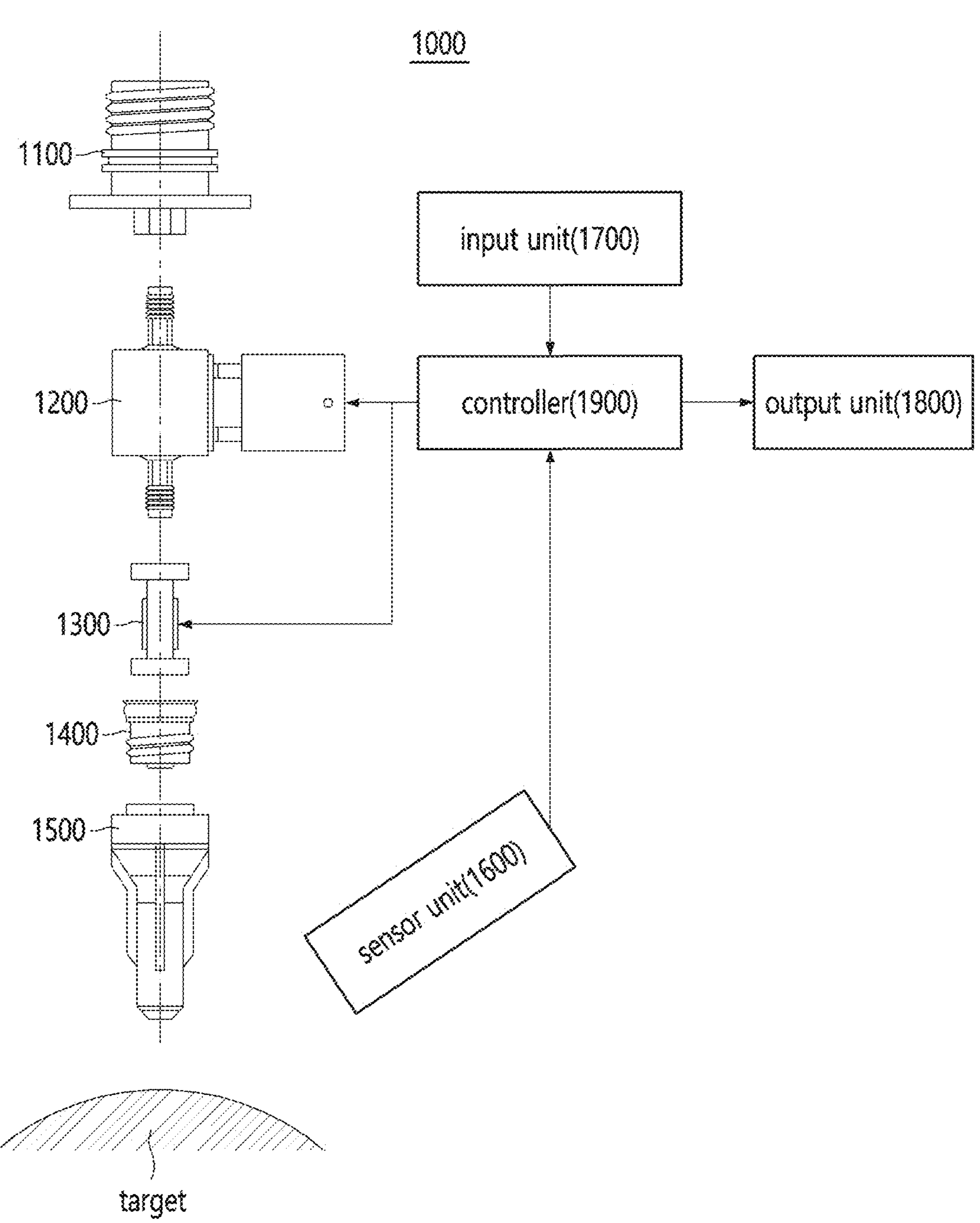
FIG. 9 is a view illustrating the components of a refrigerant spray device according to an embodiment.

FIG. 9 is a view illustrating the components of a refrigerant spray device 1000 according to an embodiment. Referring to FIG. 9, the refrigerant spray device 1000 may include a container receiving unit 1100, a flow regulating unit 1200, a heat providing unit 1300, a nozzle coupling unit 1400, a nozzle 1500, a sensor unit 1600, an input unit 1700, an output unit 1800, and a controller 1900.

The container receiving unit 1100 may accommodate a refrigerant container RC. The container receiving unit 1100 is provided with a refrigerant receiving portion into which a refrigerant is introduced. The refrigerant receiving portion may be understood as a component including a flow path or hole for movement of the refrigerant.

For example, the refrigerant container RC may be provided as a portable cartridge, and the refrigerant container RC may be mounted on or detached from the container receiving unit 1100. When the refrigerant container RC is mounted on the container receiving unit 1100, the refrigerant in the refrigerant container RC may be moved to the refrigerant receiving portion of the container receiving unit 1100.

When the refrigerant container RC is provided as a cartridge and mounted on the container receiving unit 1100, a component for perforating a cartridge inlet to enable the refrigerant to come out of the cartridge and a component for sealing the perforated cartridge inlet to prevent the refrigerant from leaking to the outside may be required. Therefore, the component for perforating and the component for sealing may be disposed between the container receiving unit 1100 and the refrigerant container RC.

For another example, the refrigerant container RC may be provided as a tank that is difficult to carry, and the container receiving unit 1100 may be connected to the refrigerant container RC through a tube. The refrigerant in the refrigerant container RC may be moved to the refrigerant receiving portion of the container receiving unit 1100 through the tube.

The flow regulating unit 1200 may control movement of the refrigerant. For example, the flow regulating unit 1200 may include a valve, and the refrigerant may or may not be moved depending on whether the valve is opened or closed. Furthermore, the degree to which the refrigerant is moved may be determined depending on the opening ratio of the valve.

Here, the valve may be a solenoid valve, but the technical idea of the present disclosure is not limited thereto.

The container receiving unit 1100 and the flow regulating unit 1200 are fluidly connected to each other so that the refrigerant introduced into the refrigerant accommodation portion of the container receiving unit 1100 is moved to the flow regulating unit 1200. For example, the refrigerant receiving portion of the container receiving unit 1100 and a flow path of the flow regulating unit 1200 may be directly connected to each other. For another example, the refrigerant receiving portion of the container receiving unit 1100 and the flow regulating unit 1200 may be connected to each other through a conduit.

As described later, the refrigerant spray device 1000 may be equipped with a precise temperature control function that precisely controls the temperature of a spray region where the refrigerant is sprayed. The heat providing unit 1300 is one of the means for implementing the precise temperature control function and may provide heat to the refrigerant before the refrigerant is sprayed.

In order to achieve the purpose of precisely controlling the temperature of the spray region, the refrigerant spray device 1000 may heat the high-pressure/low-temperature refrigerant using the heat providing unit 1300 before the refrigerant is sprayed.

The heat providing unit 1300 may include a heat source and a heat transfer medium. The heat source is a component that produces heat and may, for example, include an element that uses a thermoelectric effect such as Peltier's effect. In this case, depending on the magnitude of power or current supplied to the heat source, the amount of heat energy produced by the heat source may vary. The heat transfer medium may provide heat produced by the heat source to the refrigerant. For example, the heat transfer medium may receive heat energy from the heat source and transfer the received heat energy to the refrigerant.

The heat transfer medium may be configured in various forms. For example, the heat source may be thermally coupled to the heat transfer medium, at least one flow path for movement of the refrigerant may be formed inside the heat transfer medium, and therefore, a component that maximizes the contact area (i.e., heat transfer area) between the heat transfer medium and the refrigerant may be provided.

The flow regulating unit 1200 and the heat providing unit 1300 may be fluidly connected to each other so that the refrigerant is moved from the flow regulating unit 1200 to the heat providing unit 1300. For example, the flow path of the flow regulating unit 1200 and a flow path of the heat providing unit 1300 may be directly connected to each other. For another example, the flow regulating unit 1200 and the heat providing unit 1300 may be connected to each other through a conduit.

The refrigerant may be sprayed through the nozzle 1500. The nozzle 1500 has a flow path formed therein for the refrigerant to flow. The flow path formed in the nozzle 1500 has narrower width at other end where the refrigerant is discharged than at one end where the refrigerant enters. The refrigerant is maintained at high pressure before the refrigerant is sprayed from the other end of the nozzle 1500, and the refrigerant sprayed from the other end of the nozzle 1500 is sprayed at high velocity while expanding adiabatically and is rapidly cooled. Here, as the pressure of the refrigerant introduced into the nozzle 1500 is higher, the temperature of the adiabatically expanded refrigerant has lower temperature and high velocity. For example, when the internal pressure of the refrigerant container RC is 50 bar, the pressure of the refrigerant introduced into the nozzle 1500 may be also close to 50 bar, and the temperature of the refrigerant sprayed from the nozzle 1500 may be about −50° C. If the refrigerant of cryogenic temperature refrigerant, which has the high pressure required for high speed spray, is sprayed directly onto the skin, it may cause cell necrosis. In order to prevent skin damage such as cell necrosis, heat energy may be applied using the heat providing unit 1300 described above before the refrigerant is sprayed.

The nozzle 1500 is attachable to and detachable from the refrigerant spray device 1000. The nozzle coupling unit 1400 may be provided to attach or detach the nozzle 1500 to and from the refrigerant spray device 1000.

The composition supply device 2000 may be mounted on the nozzle 1500. For example, a part of the composition supply device 2000 may be coupled to the nozzle 1500 so that an output end of the composition guide 2100 of the composition supply device 2000 is disposed adjacent to an orifice of the nozzle 1500.

Meanwhile, the flow regulating unit 1200, the heat providing unit 1300, and the nozzle 1500 are fluidly connected to each other, and may be arranged in various ways. For example, the heat providing unit 1300 may be disposed between the flow regulating unit 1200 and the nozzle 1500 so that the refrigerant passes the flow regulating unit 1200 and reaches the heat providing unit 1300, and passes the heat providing unit 1300 and reaches the nozzle 1500. For another example, the flow regulating unit 1200 may be disposed between the heat providing unit 1300 and the nozzle 1500 so that the refrigerant passes the heat providing unit 1300 and reaches the flow regulating unit 1200, and passes the flow regulating unit 1200 and reaches the nozzle 1500.

The sensor unit 1600 may measure the temperature of the spray region where the refrigerant is sprayed. For example, the sensor unit 1600 may measure the temperature of the skin surface where the refrigerant is sprayed and provide measurement information to the controller 1900.

Meanwhile, the sensor unit 1600 may measure the temperature of a part of the components of the composition supply device 2000. For example, the sensor unit 1600 may measure the temperature of the composition guide 2100 or a mixing unit 2300 and provide measurement information to the controller 1900.

The input unit 1700 may receive a user's input. For example, the input unit 1700 may include at least one push button switch and provide a push input signal to the controller 1900 in response to the user's pressure on the switch, and the controller 1900 may control opening and closing of the flow regulating unit 1200 based on the push input signal. In addition, the input unit 1700 may include at least one rotary switch and provide a rotation input signal to the controller 1900 in response to the user's operation, and the controller 1900 may set a target temperature or target time based on the rotation input signal. Here, the target temperature refers to a temperature to be reached by adjusting the temperature of the spray region. In addition, the target time refers to a time during which spraying of the refrigerant needs to be maintained or a time during which the temperature of the spray region needs to be maintained at the target temperature. In addition, the user may use the input unit 1700 to set a target penetration depth of the composition. As described later, the mixing spray system 100 may control the size of frozen particles by controlling the heat applied to the refrigerant or the flow rate of the composition and thereby adjust the penetration depth.

The output unit 1800 may output an interface for use of the refrigerant spray device 1000 and various information to the user. For example, the output unit 1800 may include a display, and the output unit 1800 may output an interface for setting the above-described target temperature or target time through the display, and while the refrigerant spray device 1000 is operated, may output information such as a real-time temperature of the spray region measured by the sensor unit 1600 or a total time during which the refrigerant is sprayed.

The controller 1900 may control the components of the refrigerant spray device 1000. For example, the controller 1900 may control the temperature of the sprayed refrigerant by controlling the heat providing unit 1300, control the flow of the refrigerant by controlling the flow regulating unit 1200, and output specific information to the user through the output unit 1800.

The refrigerant spray device 1000 may be operated in the following manner.

First, the controller 1900 may set the target temperature and the target time. For example, the controller 1900 may provide an interface that guides the user to set the target temperature and the target time through the output unit 1800, receive a setting input signal in response to the user's operation through the input unit 1700, and set the target temperature and the target time based on the received setting input signal.

Thereafter, the controller 1900 may output a message indicating to the user that operation preparation is complete through the output unit 1800, receive a switch-on input signal in response to the user's operation through the input unit 1700, and enable the refrigerant to be sprayed based on the received switch-on input signal.

The controller 1900 may perform precise cooling on the spray region while the refrigerant is sprayed. For example, while the refrigerant is sprayed, the controller 1900 may acquire the real-time temperature of the spray region measured by the sensor unit 1600, and control the heat providing unit 1300 by comparing the obtained real-time temperature with the set target temperature. Specifically, when the obtained temperature value is lower than the target temperature, the controller 1900 may increase the heat energy applied to the refrigerant through the heat providing unit 1300, and when the obtained temperature value is higher than the target temperature, the controller 1900 may reduce the heat energy applied to the refrigerant through the heat providing unit 1300. Here, the controller 1900 may use proportional integral derivative (PID) control as a feedback control technology.

As precision cooling is performed by the controller 1900, the temperature of the spray region may be controlled within a predetermined error range based on the target temperature.

Meanwhile, the controller 1900 provide heat to the refrigerant using the heat providing unit 1300 regardless of the temperature of the spray region. For example, the controller 1900 may control the heat providing unit 1300 to provide heat energy per a predetermined unit time. In this case, temperature measurement for the spray region may not be performed.

Although not illustrated in FIG. 9, the refrigerant spray device 1000 may further include a distance maintenance unit. In spraying the refrigerant to the spray region, it is preferable that the distance between the target region and the refrigerant spray device 1000 is maintained constant. For example, it is preferable that the refrigerant and the composition are sprayed while the nozzle 1500 of the refrigerant spray device 1000 is located within a recommended spray distance range with respect to the target region.

In particular, when it is necessary to measure and monitor the temperature of the spray region in the refrigerant spray device 1000 (e.g., when feedback control is performed using the temperature of the target region, when the temperature of the target region decreases to equal to or lower than a safe temperature and the operation of the device stopped, or when the real-time temperature of the target region is output to the user), the temperature of the spray region needs to be accurately measured.

The distance maintenance unit may be located adjacent to the nozzle 1500. The distance maintenance unit may be connected to the housing of the refrigerant spray device 1000. The length of the distance maintenance unit may be designed so that the distance from the orifice of the nozzle 1500 to an end of the distance maintenance unit in a direction parallel to a central axis CA of the nozzle 1500 is within the recommended spray distance range. For example, the length of the distance maintenance unit may be determined based on a spray distance for maintaining the freeze ratio of the composition at equal to or greater than a predetermined value.

Meanwhile, the refrigerant spray device 1000 is not limited to the above-described embodiment, and any device or structure that performs the function of spraying refrigerant by coupling with the refrigerant container RC directly or indirectly through a tube may be regarded as the refrigerant spray device 1000 described in the present disclosure. For example, the refrigerant spray device 1000 may not heat the refrigerant, and therefore, the heat providing unit 1300 and the sensor unit 1600 may be omitted.

Figure 10:
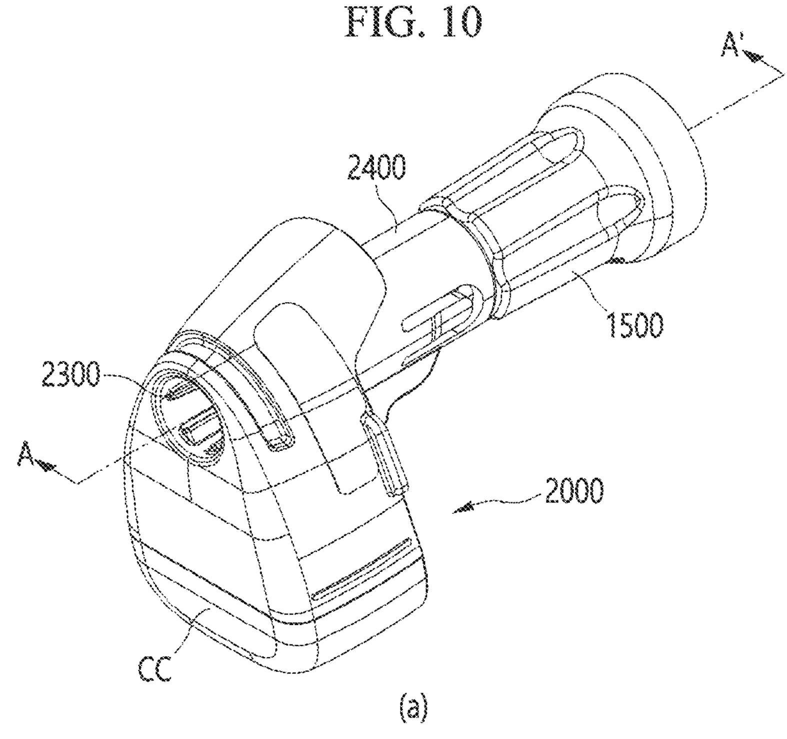
FIG. 10 is a view illustrating a composition supply device according to an embodiment.
Figure 10:
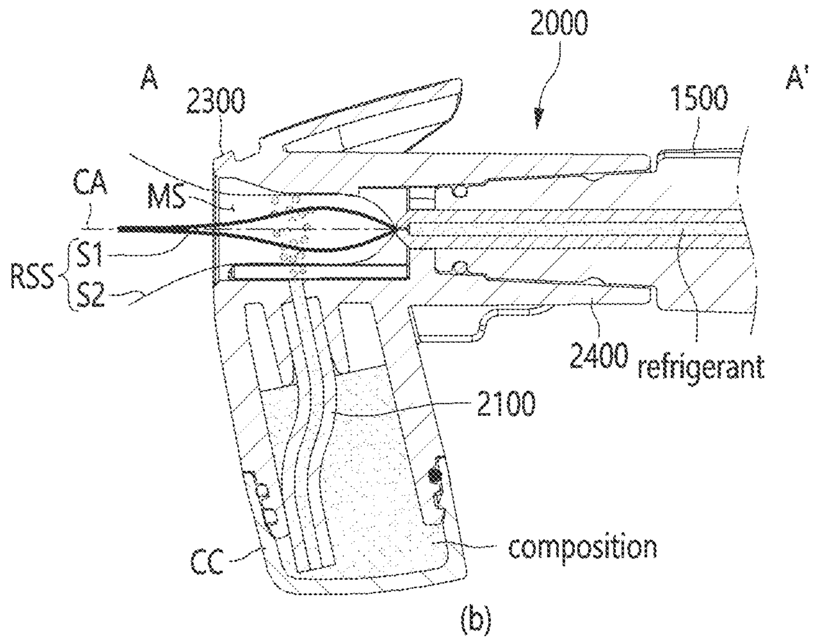

FIG. 10 is a view illustrating a composition supply device 2000 according to a first embodiment. (a) of FIG. 10 illustrates the composition supply device 2000 coupled to the nozzle 1500, and (b) of FIG. 10 illustrates a composition and a refrigerant being mixed and sprayed on a cross-section A-A' with the composition supply device 2000 coupled to the nozzle 1500.

Referring to FIG. 10, the composition supply device 2000 may include a composition guide 2100, a mixing unit 2300, a composition container CC, and a coupling part 2400.

The composition guide 2100 serves to guide movement of the composition. For example, as illustrated in (b) of FIG. 10, the composition guide 2100 may fluidly connect the composition container CC and the mixing unit 2300, and the composition stored in the composition container CC may be moved to the mixing unit 2300 through the composition guide 2100. The composition guide 2100 may be implemented in the form of a tube. The composition guide 2100 may include an input end through which the composition is introduced and an output end through which the composition is discharged.

The mixing unit 2300 provides a mixing space MS where the composition and the refrigerant are mixed. As illustrated in (b) of FIG. 10, the mixing unit 2300 has an inner surface defining the mixing space MS. The output end of the composition guide 2100 may be located on the inner surface of the mixing unit 2300. The mixing space MS may be fluidly connected to the nozzle 1500 of the refrigerant spray device 1000, and when the refrigerant is sprayed from the nozzle 1500, a refrigerant spray stream RSS may be formed in the mixing space MS.

The refrigerant spray stream RSS may be divided into a main stream S1 and a sub-stream S2. The main stream S1 may refer to a region where the refrigerant is sprayed relatively strongly, and the sub-stream S2 may refer to a region where the refrigerant is sprayed relatively weakly. Alternatively, the main stream S1 may refer to a region where the density of the refrigerant is relatively high, and the sub-stream S2 may refer to a region where the density of the refrigerant is relatively low.

The main stream S1 and the sub-stream S2 may be divided based on the central axis CA of the nozzle 1500. For example, when the refrigerant spray stream RSS is cut perpendicularly to the central axis CA of the nozzle 1500, the main stream S1 may locate within a boundary distance from the central axis CA of the nozzle 1500, and the sub-stream S2 may locate outside the boundary distance from the central axis CA of the nozzle 1500. The boundary distance may vary depending on the distance from an end of the nozzle 1500, and the internal pressure of a refrigerant container RC and the size of the orifice of the nozzle 1500. For another example, a region where the temperature of the refrigerant is equal to or lower than a threshold temperature in the refrigerant spray stream RSS may be the main stream S1, and the remaining region may be the sub-stream S2. For another example, a region where the average velocity of the refrigerant is equal to or greater than a threshold velocity in the refrigerant spray stream RSS may be the main stream S1, and the remaining region may be the sub-stream S2. For another example, a region where the density of the refrigerant is equal to or greater than a threshold density in the refrigerant spray stream RSS may be the main stream S1, and the remaining region may be the sub-stream S2.

Meanwhile, it is important that the composition is introduced into the main stream S1 of the refrigerant spray stream RSS. Because the velocity of the refrigerant is faster and the temperature thereof is lower in the main stream S1 than in the sub-stream S2, the temperature of the composition becomes lower and the spray speed of the composition is also increases when the composition meets refrigerant particles and is sprayed in the main stream S1 rather than when the composition meets refrigerant particles and is sprayed in the sub-stream S2 spray speed.

The composition container CC may store the composition therein. The composition container CC may have an injection port through which the composition is injected. The composition container CC may have a ventilation hole through which external air is introduced.

The coupling part 2400 refers to a part coupled to the nozzle 1500 in the composition supply device 2000. For example, the coupling part 2400 may include a hook coupling member, a screw coupling member, or a force-fitting coupling member, and may be coupled to and fixed to one region of the nozzle 1500.

When the refrigerant spray stream RSS is formed in the mixing space MS, the refrigerant is sprayed adjacent to the output end of the composition guide 2100, and a negative pressure is formed at the output end of the composition guide 2100 according to Bernoulli's principle. Since the composition container CC has the ventilation hole, the internal pressure thereof is maintained at atmospheric pressure. Therefore, the composition stored in the composition container CC is moved to the output end of the composition guide 2100 where a lower pressure is formed, and is consequently introduced into the refrigerant spray stream RSS.

Meanwhile, a guide plate for moving the composition to the main stream S1 of the refrigerant spray stream RSS may be installed in the mixing unit 2300. The guide plate includes a surface having a preset length. A first end of the guide plate may be disposed adjacent to the output end of the composition guide 2100, and a second end of the guide plate may be disposed adjacent to the main stream S1. Therefore, the composition introduced through the composition guide 2100 may be moved along the guide plate and reach the main stream S1.

The components of the composition supply device 2000 may be manufactured integrally. Alternatively, at least parts of the components of the composition supply device 2000 may be manufactured separately and connected to each other.

Figure 11:
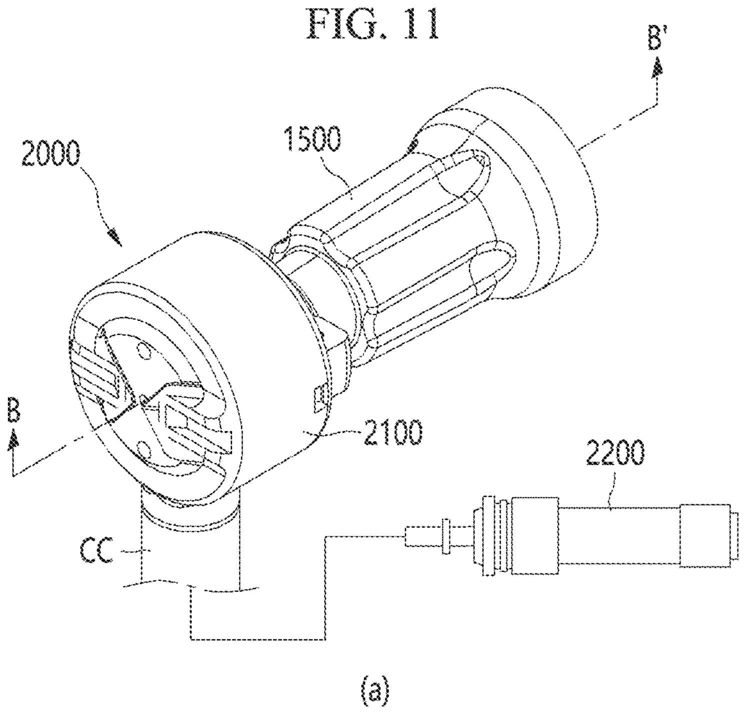
FIG. 11 is a view illustrating a composition supply device according to another embodiment.
Figure 11:
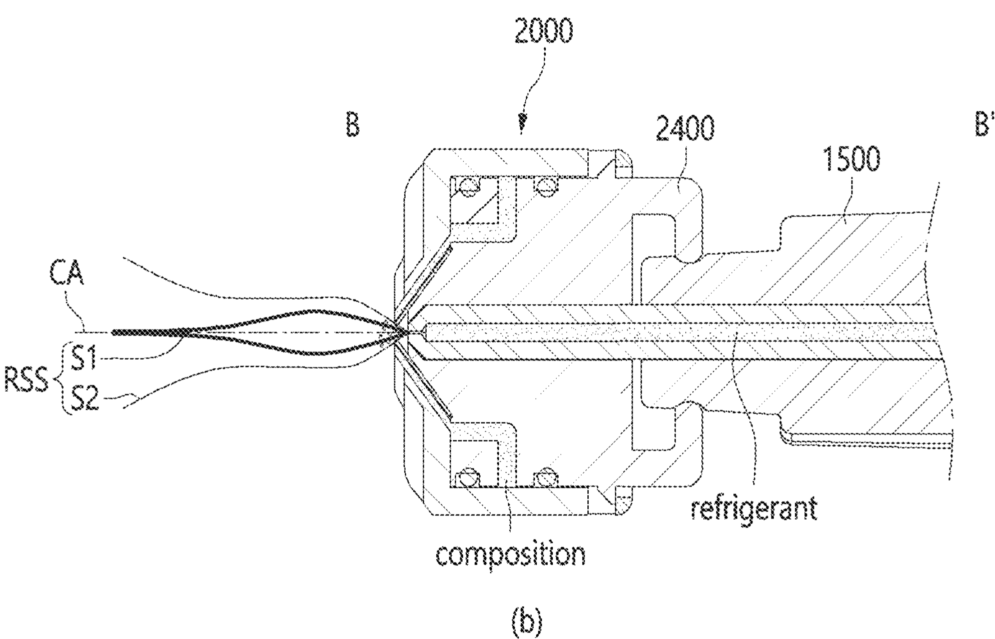

FIG. 11 is a view illustrating a composition supply device 2000 according to a second embodiment. (a) of FIG. 11 illustrates the composition supply device 2000 coupled to the nozzle 1500, and (b) of FIG. 11 illustrates a composition and a refrigerant being mixed and sprayed on a cross-section B-B' with the composition supply device 2000 coupled to the nozzle 1500.

Referring to FIG. 11, the composition supply device 2000 may include a composition guide 2100, a composition container CC, an actuator 2200, and a coupling part 2400.

The composition guide 2100 is a component that receives the composition from the composition container CC and supply the composition to a refrigerant spray stream RSS. The composition guide 2100 may include an input end through which the composition is introduced and an output end through which the composition is discharged.

Referring to (b) of FIG. 11, a composition flow path through which the composition is moved is formed inside the composition guide 2100, and the output end of the composition guide 2100 may be disposed adjacent to the orifice of the nozzle 1500. Specifically, the output end of the composition guide 2100 may be disposed to be spaced apart from the orifice of the nozzle 1500 by a first distance in a direction parallel to the central axis CA of the nozzle 1500 and by a second distance in a direction orthogonal to the central axis CA of the nozzle 1500. Here, the output end of the composition guide 2100 may be located to make contact with a main stream S1 of the refrigerant spray stream RSS formed by the nozzle 1500. For example, the first distance and the second distance may be determined based on the boundary of the main stream S1 and a sub-stream S2 of the refrigerant spray stream RSS. The positional relationship between the output end of the composition guide 2100 and the nozzle 1500 will be described later.

The composition container CC is a component that stores the composition therein. The composition container CC may have an injection port through which the composition is injected. The composition container CC may be fluidly connected to the actuator 2200. The composition inside the composition container CC may be pressurized by the actuator 2200 and moved to the composition guide 2100.

The actuator 2200 may be configured to supply a fluid to a mixing unit 2300 at a preset flow rate. The actuator 2200 may include, for example, a piston and an electric motor, and may pressurize the fluid by receiving power and moving the piston.

Since the coupling part 2400 is the same as those described above, a description thereof will be omitted.

Referring to (b) of FIG. 11, when the refrigerant spray stream RSS is formed by the refrigerant spray device 1000, the actuator 2200 of the composition supply device 2000 may be operated to pressurize the composition in the composition container CC, causing the composition to be introduced into the refrigerant spray stream RSS through the composition guide 2100. Here, the flow regulating unit 1200 and the actuator 2200 may be controlled by the controller 1900. For example, the flow regulating unit 1200 may be operated first to spray the refrigerant, and then the actuator 2200 may be operated to discharge the composition. For another example, the flow regulating unit 1200 and the actuator 2200 may be operated simultaneously.

In the above, it has been described that the refrigerant spray device 1000 and the composition supply device 2000 are manufactured separately and coupled to each other, but the technical idea of the present disclosure is not limited thereto. For example, a part of the components of the composition supply device 2000 may be mounted on the refrigerant spray device 1000, and a part of the components of the refrigerant spray device 1000 may be implemented in the composition supply device 2000. Specifically, the composition supply device 2000 may include a component that performs the function of the nozzle 1500, and the composition supply device 2000 may be coupled to the nozzle coupling unit 1400 of the refrigerant spray device 1000.

As described above, the refrigerant spray stream RSS may be formed by the refrigerant spray device 1000, and the composition may be introduced into the refrigerant spray stream RSS by the composition supply device 2000. The composition introduced into the refrigerant spray stream RSS may be broken into microparticles in the refrigerant spray stream RSS and frozen by heat exchange with the refrigerant having a relatively low temperature. Here, the size of the microparticles may be about 10 μm to about 300 μm. Alternatively, the size of the microparticles may be about 10 μm to about 100 μm.

However, as will be described later, depending on the design method and control method of the mixing spray system 100, the composition may or may not be frozen, and the freeze ratio may vary.

Factors Affecting Frozen Particle Generation

First, factors involved in whether and at what ratio the composition is frozen may include the temperature of the refrigerant spray stream RSS, composition flow rate, and composition inflow position.

As the temperature refrigerant spray stream RSS decreases, the composition may be frozen easily. Here, the temperature of the refrigerant spray stream RSS may refer to a temperature measured at a point within the refrigerant spray stream RSS (e.g., the temperature of a point spaced a predetermined distance apart from the orifice of the nozzle 1500). Alternatively, the temperature of the refrigerant spray stream RSS may refer to an average temperature of at least one region of the refrigerant spray stream RSS. As the temperature of refrigerant particles that exchange heat with the composition decreases, the temperature of the composition may decrease, thereby increasing the probability of freezing the composition. Furthermore, as the temperature of refrigerant particles decreases, the freeze ratio of the composition may increase.

Meanwhile, excessively lowering the temperature of the refrigerant spray stream RSS to freeze the composition may cause pain or irreversible damage to the skin. Therefore, the temperature of the refrigerant spray stream RSS needs to be controlled so that the composition does not cause pain or damage to the skin when frozen.

In addition, when the temperature of the refrigerant spray stream RSS excessively decreases, moisture on the skin surface may be frozen, forming substances that impede penetration, such as an ice film, and the composition may not reach the skin surface and bounce off the ice film.

The temperature of the refrigerant spray stream RSS may vary depending on the pressure before the refrigerant is sprayed from the nozzle 1500. For example, as the pressure of the refrigerant before the refrigerant is sprayed from the nozzle 1500 increases, the temperature of the refrigerant spray stream RSS may decrease. This is because as the refrigerant pressure before spraying increases, a difference with the refrigerant pressure after spraying (atmospheric pressure) increases, and temperature drop increases accordingly.

The refrigerant pressure before spraying may be substantially the same as the internal pressure of the refrigerant container RC. In other words, as the internal pressure of the refrigerant container RC increases, the refrigerant pressure before spraying may increase and the temperature of the refrigerant spray stream RSS may decrease.

Therefore, the refrigerant container RC with high internal pressure may be used to freeze the composition or increase the freeze ratio of the composition. Alternatively, the refrigerant container RC may be heated to increase the pressure of the refrigerant container RC.

Meanwhile, in order to increase the refrigerant pressure before spraying, the refrigerant spray device 1000 may further include a compressor. For example, the compressor may be disposed between the nozzle 1500 and the flow regulating unit 1200 or between the flow regulating unit 1200 and the container receiving unit 1100 to increase the pressure of the refrigerant.

The temperature of the refrigerant spray stream RSS may vary depending on the degree to which the refrigerant is heated before being sprayed from the nozzle 1500. As the amount of refrigerant heated increases, the temperature of the refrigerant spray stream RSS may increase. This is because the refrigerant temperature before spraying increases and the gas ratio in the refrigerant increases, reducing the amount of refrigerant that expands.

The amount of refrigerant heated may be adjusted by the heat providing unit 1300 of the refrigerant spray device 1000. For example, when the heat providing unit 1300 is a thermoelectric element that receives power and produces heat energy, the heat energy per unit time supplied from the heat providing unit 1300 to the refrigerant may be adjusted by adjusting the power applied to the heat providing unit 1300.

The amount of refrigerant heated may be controlled so that the temperature of the skin surface is equal to or greater than a minimum temperature that causes skin damage or pain. To this end, the controller 1900 of the refrigerant spray device 1000 may perform feedback control using a difference between the real-time temperature of the target region and the minimum temperature.

The temperature of the refrigerant spray stream RSS may be controlled using a method of controlling the refrigerant pressure before spraying, a method of controlling the heat energy applied to the refrigerant, or a combination thereof.

As the composition flow rate decreases, the composition may be frozen easily. The composition flow rate refers to an amount of composition that is introduced into the refrigerant spray stream RSS per unit time. Alternatively, the composition flow rate refers to an amount of composition that is supplied from the composition guide 2100 per unit time.

Since the composition introduced into the refrigerant spray stream RSS receives cooling energy (the temperature thereof decreases through heat exchange) by the refrigerant spray stream RSS, the cooling energy that the composition receives per unit mass decreases as the composition flow rate increases, so the composition may not be frozen or the freeze ratio may be reduced.

Meanwhile, as the composition flow rate decreases, the total amount of refrigerant used to spray a specific amount of composition to the target region may increase. That is, when the composition flow rate excessively decreases, the total amount of refrigerant used to spray the specific amount of composition may excessively increase, increasing the cost and time required for freeze spraying. Alternatively, when the composition flow rate excessively decreases and a predetermined amount of refrigerant is used, the amount of the composition sprayed may excessively decrease, thereby reducing the amount of composition penetrating into the skin.

Therefore, the composition flow rate needs to be controlled so that the composition is frozen and the amount of composition supplied is equal to or greater than a predetermined level during a predetermined treatment time.

The composition flow rate may be adjusted using the actuator 2200. For example, when supplying the composition to the composition guide 2100, the pressure applied to the composition may be controlled to be constant using the actuator 2200, and the composition flow rate may be controlled to be constant depending on the magnitude of the pressure. As the pressure applied to the composition increases, the composition flow rate increases, and as the pressure applied to the composition decreases, the composition flow rate decreases.

When the composition guide 2100 includes a conduit, the composition flow rate may be adjusted depending on the width of the conduit. Even when the composition is supplied from the composition container CC to the composition guide 2100 through the conduit, the composition flow rate may be adjusted depending on the width of the conduit. In other words, the composition flow rate may be determined depending on the width of the conduit designed when manufacturing the conduit. As the width of the conduit increases, the composition flow rate increases, and as the width of the conduit decreases, the composition flow rate decreases.

The composition flow rate may be controlled by using the actuator 2200, a method of designing the width of the conduit of the composition guide 2100 or the conduit connected to the composition guide 2100, or a combination thereof.

The closer the composition inflow position is to the nozzle 1500, the better the composition may be frozen. When spraying the composition and the refrigerant onto the skin surface using the mixing spray system 100, the composition is cooled by the refrigerant spray stream RSS from the position where it inflows into the refrigerant spray stream RSS until it reaches the skin surface.

In other words, as the distance from the position where the composition is introduced to the skin surface increases, the time it takes for the composition to be cooled by the refrigerant spray stream RSS increases, increasing the possibility of freezing or the freeze ratio of the composition. Alternatively, as the distance from the position where the composition is introduced to the orifice of the nozzle 1500 decreases, the time it takes for the composition to be cooled by the refrigerant spray stream RSS increases, increasing the possibility of freezing or the freeze ratio of the composition.

However, the composition inflow position may be understood as the position of the output end of the composition guide 2100, and when the output end of the composition guide 2100 is disposed excessively close to the orifice of the nozzle 1500, the refrigerant sprayed from the nozzle 1500 may collide with the composition guide 2100, forming turbulence. Considering stable spraying of the composition and the refrigerant and deceleration of the refrigerant spray stream RCC due to turbulence, it is preferable that no turbulence is formed.

The output end of the composition guide 2100 may be disposed to be spaced apart from the orifice of the nozzle 1500 by the first distance in a direction parallel to the central axis CA of the nozzle 1500 and by the second distance in a direction orthogonal to the central axis CA of the nozzle 1500.

The first distance may be within about 20 mm. The first distance may be, for example, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm.

The second distance may be within about 10 mm. The second distance may be, for example, 0.1 mm, 0.2 mm, 0.3 mm, 0.4 mm, 0.5 mm, 0.6 mm, 0.7 mm, 0.8 mm, 0.9 mm, or 10 mm. As described above, the first distance and the second distance decrease, the composition may be frozen easily, but when they excessively decrease, the problem of forming turbulence may occur.

For example, the composition inflow position may be determined as a position that is spaced a predetermined distance apart from the nozzle 1500 and corresponds to the edge of the main stream S1 of the refrigerant spray stream RSS formed by the nozzle 1500. In this case, the first distance and the second distance may be determined based on the boundary of the main stream S1 and the sub-stream S2 of the refrigerant spray stream RSS.

Implementation of System for Freeze Spraying

To implement the mixing spray system 100 that enables freeze spraying, the refrigerant spray stream temperature, composition flow rate, composition inflow position described above, or a combination thereof may be considered.

Fundamentally, the mixing spray system 100 needs to be implemented so that the composition is frozen on the skin surface. To achieve this, the temperature of the refrigerant spray stream RSS formed in the mixing spray system 100 needs to be equal to or less than the freezing point of the composition. In particular, the temperature of the refrigerant spray stream RSS at a position or region where the composition is introduced needs to be equal to or less than the freezing point of the composition. For example, the freezing point of the composition may be about −30° C. to about 0° C. In this case, the temperature of the refrigerant spray stream RSS may be controlled to be equal to or less than about −50° C. or about −30° C. at the position where the composition is introduced.

The mixing spray system 100 needs to be implemented so that the freeze ratio of the composition on the skin surface is equal to or greater than a target freeze ratio. The target freeze ratio refers to a ratio of the solid composition to the composition that reaches the skin surface. Here, the target freeze ratio may be calculated according to the above-described freeze ratio calculation methods.

The target freeze ratio may be determined through freeze spraying experiments. For example, as described later, an effective ratio range in which the penetration effect of the composition is significant may be calculated by conducting an experiment on freeze spraying, and the target freeze ratio may be selected within the effective ratio range. For example, through the first experiment which will be described later, a significant penetration effect was confirmed when the freeze ratio was 17% or 5%, and through the second experiment which will be described later, it was confirmed that the penetration effect increased as the freeze ratio increased, so the target freeze ratio may be determined as equal to or greater than 17%. Alternatively, the target freeze ratio may be determined as equal to or greater than 5%. The target freeze ratio needs to be set as high as possible, but limitations (e.g., prevention of skin damage, prevention of ice film formation, etc.) which will be described later may be further considered.

The composition supply device 2000 may be designed to have an appropriate composition flow rate (e.g., a target flow rate) in consideration of the freeze ratio of the composition. Here, the target flow rate may be a composition flow rate that needs to be sprayed for a predetermined period of time. The pressure that needs to be provided by the actuator 2200 may be specified based on the determined target flow rate. Alternatively, the width of the conduit included in the composition guide 2100 or the width of the conduit connected to the composition guide 2100 may be determined based on the determined target flow rate.

The composition supply device 2000 may be designed to have an appropriate target inflow position for the composition in consideration of the freeze ratio of the composition. That is, the positional relationship between the refrigerant spray device 1000 and the composition supply device 2000 may be specified to determine the appropriate target inflow position of the composition. As described above, the target inflow position may be determined as a position adjacent to the nozzle 1500 and where vortex formation is minimized based on the orifice of the nozzle 1500. The positional relationship between the nozzle 1500 and the composition guide 2100 of the refrigerant spray device 1000 may be specified depending on the target inflow position. Specifically, the output end through which the composition is discharged from the composition guide 2100 may be designed to be located at the target inflow position based on the orifice of the nozzle 1500.

The refrigerant spray device 1000 may be designed so that the refrigerant has an appropriate temperature in consideration of the freeze ratio of the composition. For example, when spraying the composition and the refrigerant from the mixing spray system 100, the heat providing unit 1300 may be controlled so that a calculated freeze ratio is equal to or greater than the target freeze ratio. Specifically, when determining the freeze ratio of the composition in the observing region OR of the refrigerant spray stream RSS while changing the heat energy per unit time produced by the heat providing unit 1300 using the controller 1900, an operating range of the heat providing unit 1300 where the freeze ratio is equal to or greater than the target freeze ratio may be specified.

Here, when the heat providing unit 1300 is implemented as a thermoelectric element, the operating range may refer to a power range that needs to be applied to the heat providing unit 1300. Also, here, when the heat providing unit 1300 is implemented as a thermoelectric element and the controller 1900 applies power to the thermoelectric element through feedback control using a preset target temperature and a real-time temperature of the skin surface, the operating range may refer to a range of the target temperature that needs to be set.

The controller 1900 may control the heat providing unit 1300 so that the heat providing unit 1300 is operated within a specified operating range. For example, the controller 1900 may apply power to the heat providing unit 1300 within a preset power range. The preset power range may refer to a range in which the freeze ratio is 5% to 100%. Alternatively, the preset power range may refer to a range in which the freeze ratio is 17% to 100%. Alternatively, the preset power range may refer to a range in which the freeze ratio is 48% to 100%. Alternatively, the preset power range may refer to a range in which the freeze ratio is 71% to 100%.

Meanwhile, the operating range of the heat providing unit 1300 may be specified by further considering a range in which the temperature of the refrigerant spray stream RSS does not cause pain or damage to the skin surface. For example, when spraying the composition and the refrigerant from the mixing spray system 100 onto the skin surface, the heat providing unit 1300 may be determined so that the temperature of the skin surface is equal to or greater than the safe temperature. The safe temperature may be determined within a range of about −10° C. to about 20° C. For example, the safe temperature may be −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C.

Furthermore, the operating range of the heat providing unit 1300 may be specified by further considering a range in which an ice film, which a penetration-impeding substance, is not formed on the skin surface by the refrigerant spray stream RSS. For example, when the composition and the refrigerant are sprayed onto the skin surface from the mixing spray system 100, the operating range of the heat providing unit 1300 may be determined so that the temperature of the skin surface is equal to or greater than an ice film forming temperature. Since the ice film may be formed when the skin surface is equal to or less than 0° C., the ice film forming temperature is 0° C.

Meanwhile, the controller 1900 may not operate the heat providing unit 1300 or the heat providing unit 1300 may be omitted from the mixing spray system 100. Specifically, as the composition having room temperature is introduced into the refrigerant spray stream RSS, the temperature of the refrigerant spray stream RSS may increase. This is because when the temperature of the refrigerant spray stream RSS is increased above the safe temperature and/or ice film forming temperature by the introduced composition, not heating the refrigerant before spraying may increase the possibility of freezing or the freeze ratio of the composition.

The refrigerant pressure may be controlled to control the temperature of the refrigerant spray stream RSS.

First, the internal pressure of the refrigerant container RC used in the mixing spray system 100 may be selected appropriately in consideration of the freeze ratio of the composition. For example, the internal pressure of the refrigerant container RC may be determined within a range of 10 bar to 1,000 bar. Preferably, the internal pressure of the refrigerant container RC is determined within a range of 30 bar to 200 bar.

The internal pressure of the refrigerant container RC may be determined in consideration of the target freeze ratio and the safe temperature. For example, the internal pressure of the refrigerant container RC may be determined between a minimum pressure value at which the freeze ratio of the composition becomes the target freeze ratio and a maximum pressure value at which the temperature of the skin surface becomes the safe temperature.

Meanwhile, the refrigerant pressure may be controlled by the separate compressor described above and/or a container heater that heats the refrigerant container RC. The compressor or container heater may control the refrigerant pressure before spraying to a pressure range determined based on the target freeze ratio and the safe temperature.

In the above, in implementing the mixing spray system 100 for freeze spraying, it has been described that the composition flow rate, the composition inflow position, and the refrigerant spray stream temperature are sequentially considered. However, the technical idea of the present disclosure is not limited thereto, and the mixing spray system 100 may be designed so that these factors are considered in a different order.

Consequently, the mixing spray system 100 to be implemented includes the refrigerant container RC that stores the refrigerant at a pressure of at least 30 bar to 200 bar, the refrigerant receiving part that receives the refrigerant from the refrigerant container RC, a nozzle 1500 having the orifice of a preset size, the composition guide 2100 disposed adjacent to the nozzle 1500 (the output end of the composition guide 2100 is located within a preset distance from the orifice of the nozzle 1500), the flow regulating unit 1200, and the controller 1900. Here, the freeze ratio of the composition in the observing region OR, which is located to be spaced apart from the orifice of the nozzle 1500 by the observing distance OD and has the observing width OW, is equal to or greater than the target freeze ratio. The mixing spray system 100 may further include the distance maintenance unit, and the distance maintenance unit may have a length within the recommended spray distance range to ensure that the freeze ratio of the composition is equal to or greater than the target freeze ratio.

In the above, the mixing spray system 100 implemented to enable freeze spraying has been described. The mixing spray system 100 implemented so that at least a part of the composition is frozen and reaches the skin surface may also be called a freeze spray system.

Spraying Composition after Freezing

The mixing spray system 100 described above sprays the composition together with the refrigerant so that the composition is frozen by the refrigerant during spraying. However, a system that performs freeze spraying cannot be implemented by simply spraying a mixture of the composition and the refrigerant, and any system may be used for freeze spraying as long as it enables the frozen composition to reach the skin surface. For example, a system that freezes the composition in advance and sprays the frozen composition may be used. Specifically, a system that freezes the composition in advance to generate frozen particles and then sprays the frozen particles onto the skin surface using a transfer medium such as compressed air may be used.

Freeze Spray Method

Hereinafter, the freeze spray method using the mixing spray system 100 will be described with reference to FIG. 12.

Figure 12:
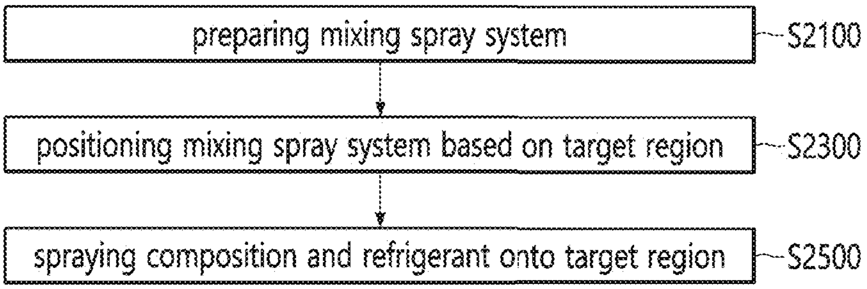
FIG. 12 is a flowchart illustrating a freeze spray method according to an embodiment.

FIG. 12 is a flowchart illustrating a freeze spray method according to an embodiment.

Referring to FIG. 12, the freeze spray method includes preparing a mixing spray system 100 (S1100), positioning the mixing spray system 100 based on a target region (S1300), and spraying a composition and a refrigerant together on the target region using the mixing spray system 100 (S1500).

Hereinafter, each step will be described in detail.

First, a user (or operator) may prepare the mixing spray system 100 (S1100). The mixing spray system 100 includes at least a nozzle 1500 for forming a refrigerant spray stream RSS and a composition guide 2100 disposed adjacent the nozzle 1500. The mixing spray system 100 may include other components described above in addition to the nozzle 1500 and the composition guide 2100.

The user may position the mixing spray system 100 based on the target region (S1300).

For example, the user may position the nozzle 1500 of the mixing spray system 100 at a predetermined distance from the target region.

Here, the predetermined distance may refer to the shortest distance between an orifice of the nozzle 1500 and the target region. The predetermined distance may be substantially the same as the recommended spray distance described above. When the recommended spray distance is presented as a range, the predetermined distance may be included within the recommended spray distance range.

Also, here, a central axis CA of the nozzle 1500 may have a preset angle with respect to the target region. For example, the angle formed between the central axis CA of the nozzle 1500 and a plane including the target region or a virtual plane in contact with the target region may have a value of about 45° to about 90°.

The user may spray the composition and the refrigerant together on the target region using the mixing spray system 100 (S1500). For example, when the user manipulates an input unit 1700 provided in the mixing spray system 100, a flow regulating unit 1200 may be opened and an actuator 2200 may pressurize the composition, causing the refrigerant and the composition to be sprayed together on the target region. In a case where the mixing spray system 100 does not include the actuator 2200, when the user manipulates the input unit 1700 (e.g., when the user presses a spray start button), the flow regulating unit 1200 may be opened to form a refrigerant spray stream RSS, and the composition may be introduced into the refrigerant spray stream RSS and sprayed due to negative pressure.

When the mixing spray system 100 is operated, the composition stored in a liquid state is introduced into the refrigerant spray stream RSS. Due to the refrigerant spray stream RSS, the composition in a liquid state is broken into microparticles, and at the same time, transitions into a solid state in the form of frozen microparticles as the temperature thereof is lowered. The composition in a solid state is accelerated in an acceleration section of the refrigerant spray stream RSS, and reaches the target region. In addition, when the mixing spray system 100 is viewed from the side at a time point at which the mixing spray system 100 is operated, an observing region OR that is spaced apart by an observing distance OD corresponding to the predetermined distance from the orifice of the nozzle 1500 and has an observing width OW, may be specified, and a freeze ratio in the observing region OR may be 5%.

Confirmation of Penetration Effect of Freeze Spraying

Hereinafter, a skin penetration effect of freeze spraying will be described through experiments on freeze spraying.

Experiments Related to Freeze Spraying

The present applicant conducted various experiments related to freeze spraying, and the experiments conducted included an experiment on the penetration effect depending on freezing and an experiment on the penetration effect depending on the freeze ratio.

First, the first experiment that confirmed the penetration effect depending on freezing will be described.

The purpose of the first experiment was to confirm that the penetration effect varies depending on whether a composition is frozen.

In the first experiment, the penetration effect was compared between a case where the composition was sprayed on the skin surface in a non-frozen state (test group 1), a case where the composition was sprayed on the skin surface in a partially frozen state (test group 2 and test group 4), and a case where the composition was sprayed on the skin surface in a mostly frozen state (test group 3).

As a target to which the composition was sprayed, human-derived skin tissue was used. Specifically, facial skin tissue discarded after surgery was used.

In control group, human-derived skin tissue was cut into a predetermined size (2 cm*2 cm) and the composition was applied thereon. The composition included acetyl hexapeptide-8-FITC combined with a fluorescent substance (fluorescein isothiocyanate, FITC) to confirm the penetration effect.

Then, after 24 hours, a fluorescence image of the cross-section of the human-derived skin tissue was captured, and the intensity and penetration depth of the fluorescent substance located under the epidermis were measured.

In test group 1, human-derived skin tissue was cut to a predetermined size and the composition was sprayed thereon without freezing. The composition included antifreeze (PG) to prevent freezing by a refrigerant, and acetyl hexapeptide-8-FITC combined with a fluorescent substance (FITC) to confirm the penetration effect.

The above-described mixing spray system 100 was used to spray the composition. Specifically, the refrigerant spray device 1000 described above and the composition supply device 2000 according to the second embodiment were used. For the mixing spray system 100 used, the freeze ratio was calculated to be 0%.

Then, after 24 hours, a fluorescence image of the cross-section of the human-derived skin tissue was captured, and the intensity and penetration depth of the fluorescent substance located under the epidermis were measured.

In test group 2, human-derived skin tissue was cut to a predetermined size, and only a part of the composition was frozen and sprayed thereon. The composition included acetyl hexapeptide-8-FITC combined with a fluorescent substance (FITC) to confirm the penetration effect.

The above-described mixing spray system 100 was used to spray the composition. Specifically, the refrigerant spray device 1000 described above and the composition supply device 2000 according to the second embodiment were used. For the mixing spray system 100 used, the freeze ratio was calculated to be 17% (within a measurement error of 5%, about 12% to about 22%).

Then, after 24 hours, a fluorescence image of the cross-section of the human-derived skin tissue was captured, and the intensity and penetration depth of the fluorescent substance located under the epidermis were measured.

In test group 3, human-derived skin tissue was cut to a predetermined size, and most of the composition was frozen and sprayed thereon. The composition included acetyl hexapeptide-8-FITC combined with a fluorescent substance (FITC) to confirm the penetration effect.

The above-described mixing spray system 100 was used to spray the composition. Specifically, the refrigerant spray device 1000 described above and the composition supply device 2000 according to the second embodiment were used. For the mixing spray system 100 used, the freeze ratio was calculated to be 100% (within a measurement error of 1%, about 99% to about 100%).

Then, after 24 hours, a fluorescence image of the cross-section of the human-derived skin tissue was captured, and the intensity and penetration depth of the fluorescent substance located under the epidermis were measured.

In test group 4, human-derived skin tissue was cut to a predetermined size, and only a part of the composition was frozen and sprayed thereon. The composition included acetyl hexapeptide-8-FITC combined with a fluorescent substance (FITC) to confirm the penetration effect.

The above-described mixing spray system 100 was used to spray the composition. Specifically, the refrigerant spray device 1000 and the composition supply device 2000 according to the first embodiment were used. For the mixing spray system 100 used, the freeze ratio was calculated to be 5% (within a measurement error of 1%, about 4% to about 6%).

Then, after 24 hours, a fluorescence image of the cross-section of the human-derived skin tissue was captured, and the intensity and penetration depth of the fluorescent substance located under the epidermis were measured.

The present applicant conducted the second experiment to confirm the penetration effect depending on the freeze ratio.

The purpose of the second experiment was to confirm that the penetration effect varies depending on the freeze ratio.

In the second experiment, a composition was sprayed on the skin surface in a frozen state, and the penetration effect was compared between a case where the freeze ratio of the composition was 5% (within a measurement error of 1%, about 4% to about 6%) (test group 1), a case where the freeze ratio of the composition was 17% (within a measurement error of 5%, about 12% to about 22%) (test group 2), a case where the freeze ratio of the composition was 48% (within a measurement error of 3%, about 45% to about 51%) (test group 3), a case where the freeze ratio of the composition was 71% (within a measurement error of 3%, about 68% to about 74%) (test group 4), and a case where the freeze ratio of the composition was 100% (within a measurement error of 1%, about 99% to about 100%) (test group 5).

The mixing spray system 100 according to the second embodiment was used to spray the composition.

As a method of adjusting the freeze ratio, a method of adjusting the heat energy applied to a refrigerant before spraying from the heat providing unit 300 of the mixing spray system 100 was adopted.

More specifically, the heat providing unit 1300 included a thermoelectric element and the power applied to the thermoelectric element was adjusted. As the heat energy applied before the refrigerant was sprayed through the nozzle 1500 changed, the temperature of a refrigerant spray stream RSS formed in the nozzle 1500 changed, and the freeze ratio of the composition changed accordingly.

Here, the applied power was adjusted using a pulse width modulation (PWM) method, and the heating power applied using the PWM method was divided into levels from 0 to 999. From test group 1 to test group 5, the freeze ratio was adjusted by varying the heating power applied to the thermoelectric element.

In the second experiment, hydrogel was used as a target to which the composition and the refrigerant were sprayed, and the penetration effect was compared by the number of holes formed in the hydrogel. The number of holes formed in the hydrogel was determined with the naked eye, and it was determined that as the number of holes formed after the composition and the refrigerant were sprayed on the hydrogel for a predetermined period of time increased, the penetration effect increased.

Experimental Results and Analysis

Hereinafter, the results of the first and second experiments will be described with reference to FIGS. 13 to 16.

Figure 13:
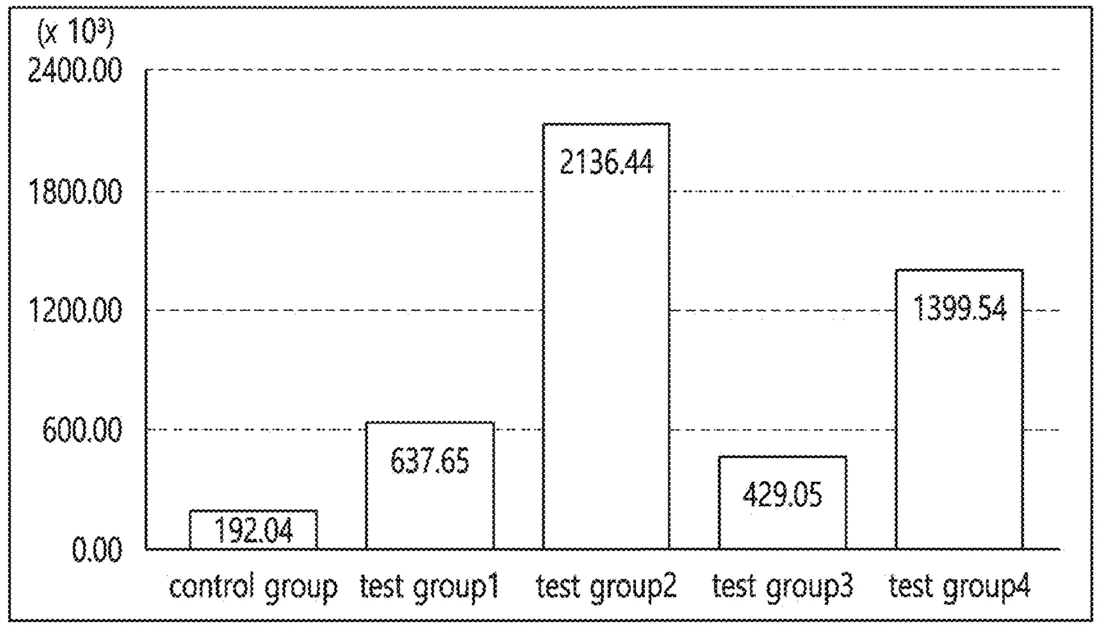
FIGS. 13 and 14 are views illustrating the results of a first experiment to confirm the penetration effect depending on freezing and the penetration effect depending on the freeze ratio.
Figure 14:
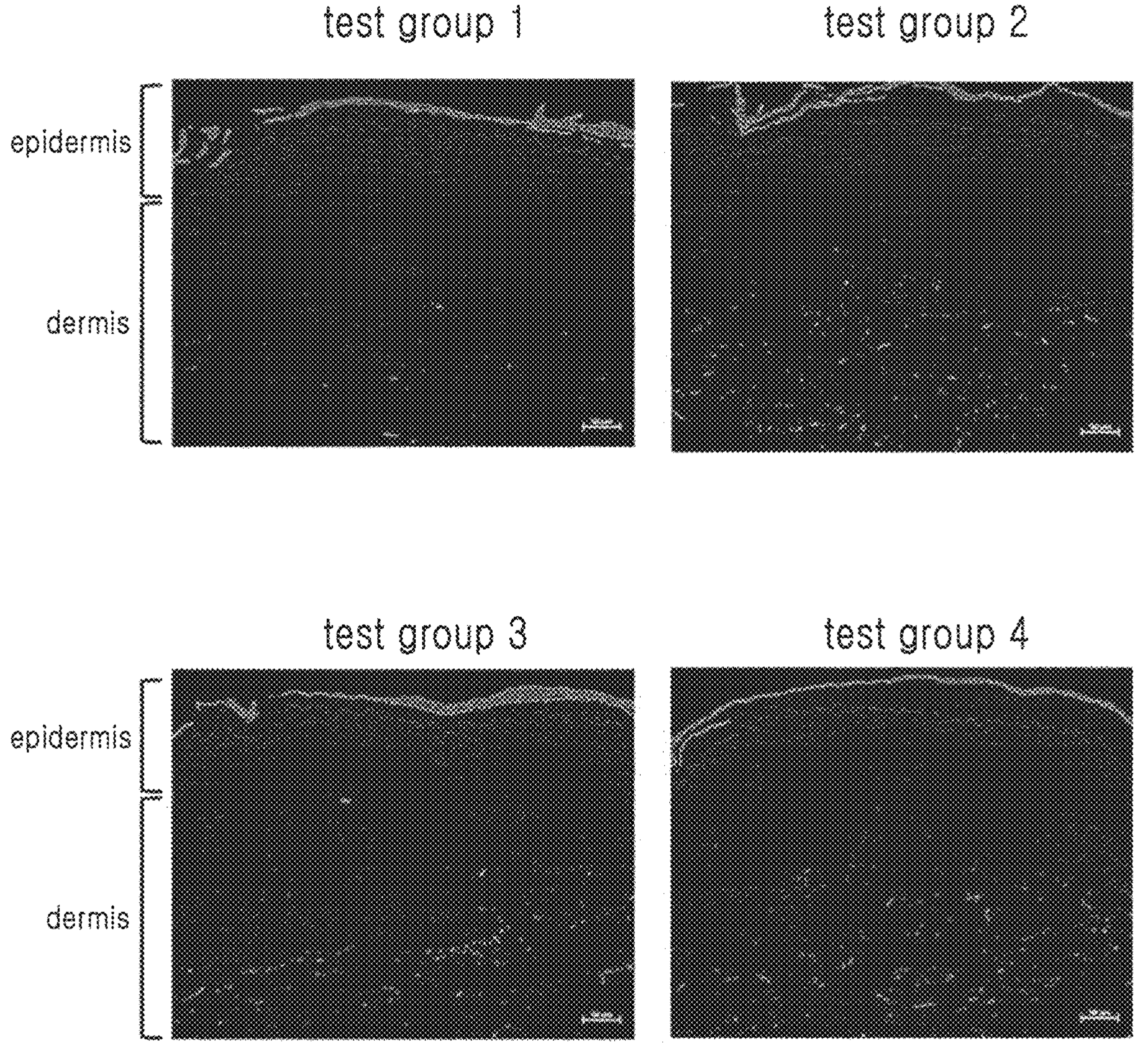

FIGS. 13 and 14 are views illustrating the results of the first experiment to confirm the penetration effect depending on freezing and the penetration effect depending on the freeze ratio.

According to the results of the first experiment, the penetration effect when the composition was sprayed in a frozen state (test group 2 and test group 4) was significantly higher than the penetration effect when the composition was sprayed in a non-frozen state (test group 1).

Referring to FIG. 13, the fluorescence intensity was 192.04 in control group and 637.65 in test group 1, while the fluorescence intensity was 2136.44 in test group 2 and 1399.54 in test group 4. Compared to test group 1, it is understood that the penetration effect improved by about 3.35 times in test group 2, and by about 2.19 times in test group 4.

Furthermore, when observing a fluorescence image of the cross-section of skin tissue in each case, as illustrated in FIG. 14, it was confirmed that the amount of composition penetrated was significantly increased in test group 2 and test group 4 compared to test group 1.

Meanwhile, in test group 3, the fluorescence intensity was measured at 429.05, which was lower than that of test group 1. This is because, as described above, the low temperature of the sprayed refrigerant caused an ice film to be formed on the surface of human-derived skin tissue, and as a result, a large amount of frozen particles did not reach the skin tissue surface. It is expected that the ice film will not be formed in areas where body heat exists, such as human skin, and therefore, the penetration effect is expected to be high when the conditions of test group 3 are applied to human skin.

Figure 15:
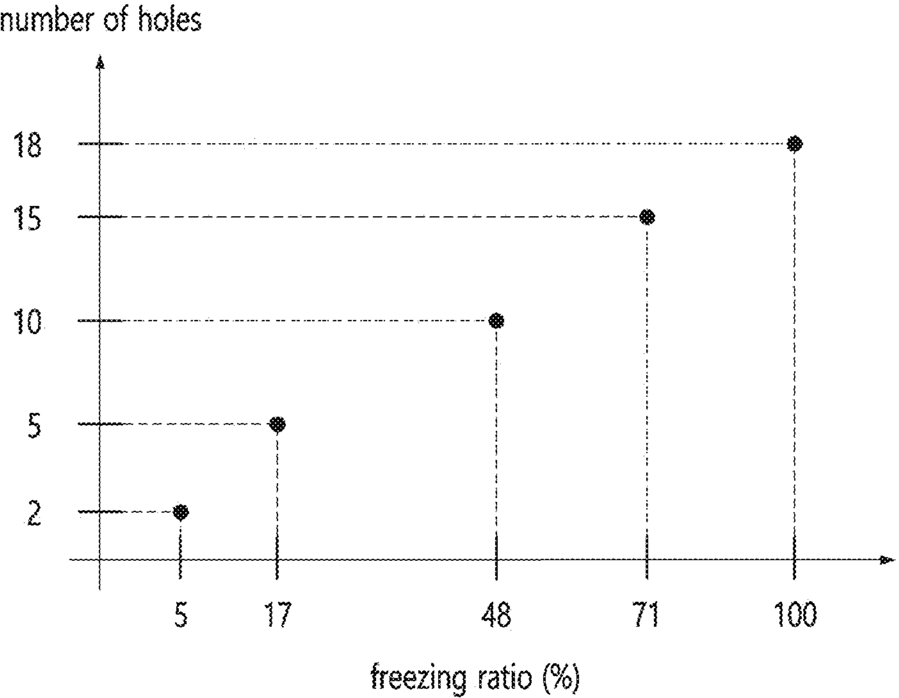
FIG. 15 is a view illustrating the results of a second experiment to confirm the penetration effect depending on the freeze ratio.
Figure 16:
FIG. 16 is a view illustrating the penetration effect of test group 1 and test group 5 in the second experiment.
Figure 16:
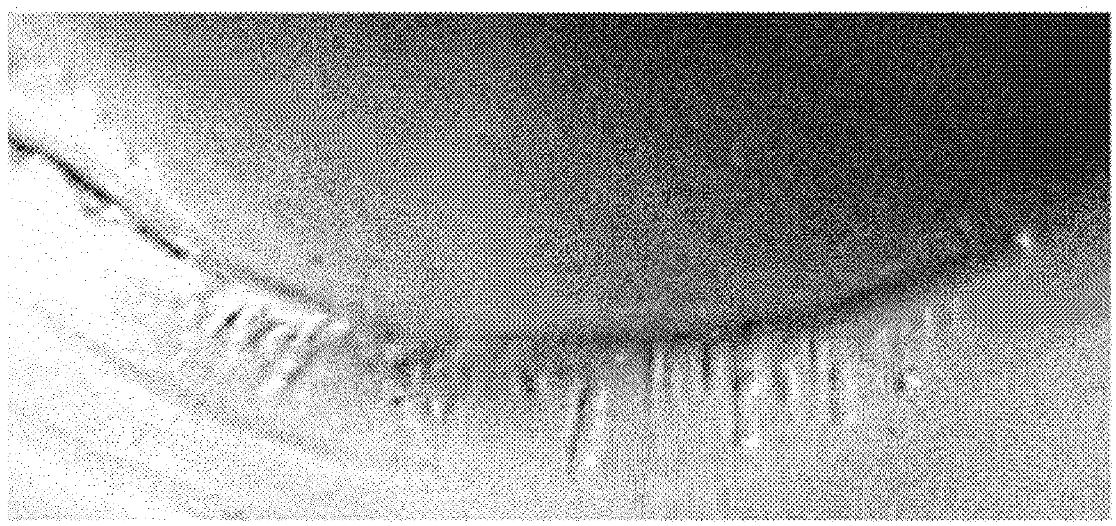

FIG. 15 is a view illustrating the results of the second experiment to confirm the penetration effect depending on the freeze ratio. FIG. 16 is a view illustrating the penetration effect of test group 1 and test group 5 in the second experiment.

As a result of the second experiment, it was confirmed that the penetration effect improved as the freeze ratio increased.

Referring to FIG. 15, the number of holes was 2 when the freeze ratio was 5%, the number of holes was 5 when the freeze ratio was 17%, the number of holes was 10 when the freeze ratio was 48%, the number of holes was 15 when the freeze ratio was 71%, and the number of holes was 18 when the freeze ratio was 100%. This thus confirmed that the number of holes increased as the freeze ratio increased. As a result, it can be understood that the penetration effect improves as the freeze ratio increases.

The penetration effect can also be confirmed with the naked eye. As illustrated in FIG. 16, the number of holes formed in the hydrogel in test group 5 was significantly increased compared to test group 1.

Based on the first experiment and the second experiment, an effective ratio range for freeze spraying may be set. According to the first experiment, the penetration effect of the composition was significant when the freeze ratio of the composition was 5% and 17%. In addition, according to the second experiment, the penetration effect improved when the freeze ratio of the composition was 17% compared to when the freeze ratio was 5%, the penetration effect improved when the freeze ratio of the composition was 48% compared to when the freeze ratio was 17%, the penetration effect improved when the freeze ratio of the composition was 71% compared to when the freeze ratio was 48%, and the penetration effect improved when the freeze ratio of the composition was 100% compared to when the freeze ratio was 71%.

Therefore, the effective ratio range may be 5% to 100%. Alternatively, the effective ratio range may be 5% to 17%. Alternatively, the effective ratio range may be 5% to 48%. Alternatively, the effective ratio range may be 5% to 71%. Alternatively, the effective ratio range may be 17% to 48%. Alternatively, the effective ratio range may be 17% to 71%. Alternatively, the effective ratio range may be 17% to 100%. Alternatively, the effective ratio range may be 48% to 71%. Alternatively, the effective ratio range may be 48% to 100%. Alternatively, the effective ratio range may be 71% to 100%.

Considering the measurement error range, the effective ratio range may be 2% to 100%. Alternatively, the effective ratio range may be 2% to 22%. Alternatively, the effective ratio range may be 2% to 51%. Alternatively, the effective ratio range may be 2% to 74%. Alternatively, the effective ratio range may be 12% to 51%. Alternatively, the effective ratio range may be 12% to 74%. Alternatively, the effective ratio range may be 12% to 100%. Alternatively, the effective ratio range may be 45% to 74%. Alternatively, the effective ratio range may be 45% to 100%. Alternatively, the effective ratio range may be 68% to 100%.

The mixing spray system 100 may be designed so that the freeze ratio of the sprayed composition is within the effective ratio range.

Control of Freeze Spraying Characteristics

In the above, the meaning of freeze spraying, the mixing spray system 100 for performing the freeze spray method, and the confirmation of the penetration effect through freeze spraying-related experiments has been described.

In freeze spraying, frozen particles of the composition may have the following characteristics: particle size and spray speed. These characteristics may be important control factors in commercializing the mixing spray system 100 that performs freeze spraying.

For a composition having a specific viscosity and surface tension, the size of frozen particles of the composition may be controlled by the temperature of the refrigerant spray stream RSS, the flow rate of the refrigerant spray stream RSS, and the composition flow rate. In addition, the size of the frozen particles may be controlled by the shape of the output end of the composition guide 2100 where the composition is located immediately before the composition is introduced into the refrigerant spray stream RSS. For example, the output end of the composition guide 2100 may have a blunt or pointed shape, and the size of the frozen particles of the composition may be larger in the blunt shape than in the pointed shape.

Control of Frozen Particle Size in Freeze Spraying

Frozen particles formed by freezing the liquid composition have a particle size. As the size of the frozen particles of the composition decreases, the mass of the refrigerant in the refrigerant spray stream RSS increases relative to the mass of the composition that has an initial velocity of substantially zero immediately after the composition is introduced into the refrigerant spray stream RSS. This means that according to the law of conservation of momentum, as the size of the frozen particles of the composition decreases, the velocity of the frozen particles of the composition increases. However, when the size of the frozen particles of the composition excessively decreases, an increase in the surface area relative to the momentum may increase air resistance. As a result, deceleration of the spray speed may increase while the solid composition reaches the skin surface.

Figure 17:
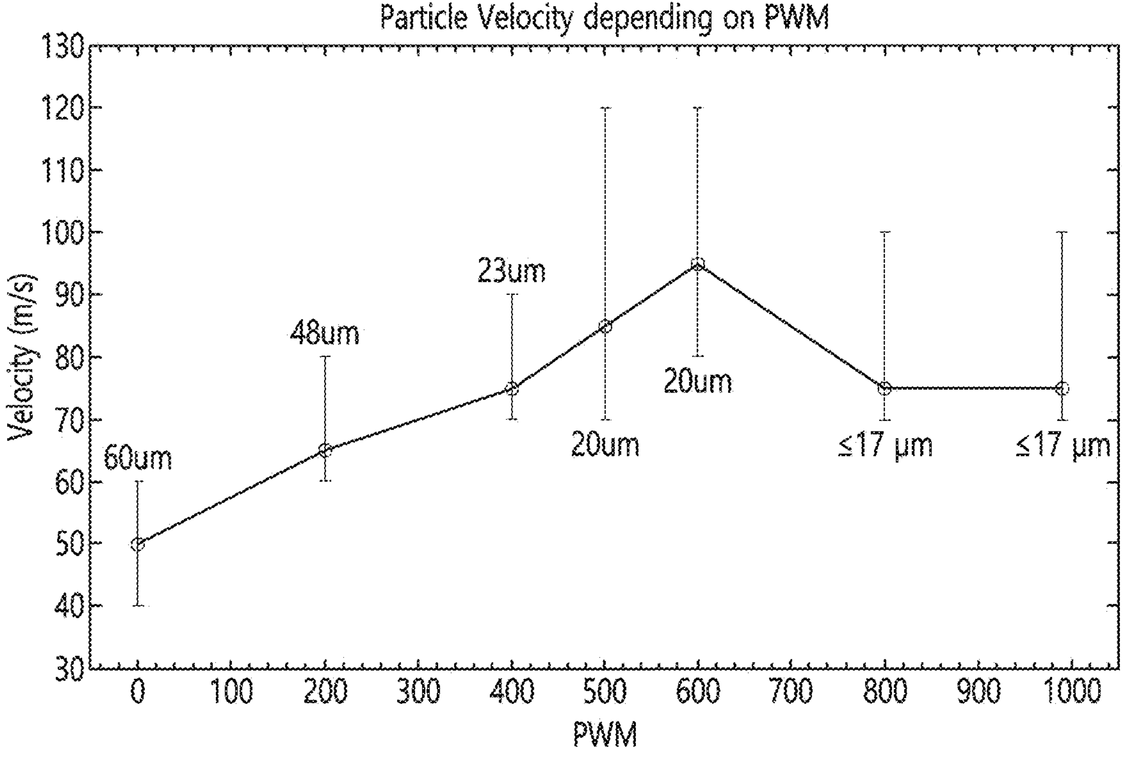
FIG. 17 is a view illustrating the relationship between particle size and spray speed according to an embodiment.

FIG. 17 is a view illustrating the relationship between particle size and spray speed according to an embodiment. The frozen particle size indicated at each point of the graph in FIG. 17 refers to the average particle size of at least a part of frozen particles of the composition. In obtaining the graph illustrated in FIG. 17, the mixing spray system 100 according to the second embodiment was used, and PWM control was used as a method of controlling the frozen particle size of the composition. Specifically, as the level of heating power applied through the PWM method increased, the frozen particle size of the composition decreased.

Referring to FIG. 17, it can be seen that the speed of the frozen particles of the composition increased as the particle size of the composition decreased, but when the particle size of the composition decreased to equal to or less than a predetermined level, the velocity of the frozen particles of the composition decreased.

Therefore, the size of the frozen particles of the composition may be set based on the point at which the velocity of the frozen particles of the composition is maximum. For example, the mixing spray system 100 may be designed so that the average size of the frozen particles of the composition is equal to or less than about 60 μm or is close to about 20 μm. For another example, when considering the direction of increasing the freeze ratio of the composition, the mixing spray system 100 may be designed so that the average size of the frozen particles of the composition is equal to or less than about 150 μm or is close to about 70 μm. As another example, the mixing spray system 100 may be designed so that the average size of the frozen particles of the composition is within about 20 μm to about 60 μm, about 20 μm to about 100 μm, about 10 μm to 60 μm, or about 10 μm to 300 μm.

In the above, the average size of the frozen particles refers to the average size of the composition particles frozen in the refrigerant spray stream RSS. However, the above-described method of calculating the average size of the frozen particles of the composition in the observing region OR may be used as a method of calculating the average size of the frozen particles of the composition.

Here, the above-described method of controlling the temperature of the refrigerant spray stream RSS may be used as a method of controlling the frozen particle size. For example, the frozen particle size of the composition may be controlled by controlling the degree to which the refrigerant is heated by the heat providing unit 1300 before being sprayed.

Meanwhile, the particle size of the frozen composition (or solid composition) excessively increases, the frozen particles may stimulate pain points when sprayed on the skin surface, causing pain. Specifically, pain may be caused when the size of the frozen particles is excessively larger than the size of skin cells (about 30 μm) or the size of pores on the skin surface (about 20 μm to about 50 μm). Therefore, the mixing spray system 100 may be designed so that the size of the frozen particles is less than about 20 μm to about 50 μm.

The size of the frozen particles of the composition may be controlled to control the skin penetration depth of the composition.

The frozen particles melt due to body heat after penetrating into the epidermis. Since the melting time varies depending on the size of the frozen particles, the position where the composition melts within the skin varies. By controlling the size of the frozen particles, the position where the composition melts may be controlled, and the depth where the composition penetrates may be controlled accordingly.

For example, at the same velocity condition, as the size of the frozen particles increases, the penetration depth may increase, and as the size of the frozen particles decreases, the penetration depth may decrease. Therefore, after determining the target penetration depth and specifying the frozen particle size range corresponding to the determined penetration depth, at least one of the level of heating power applied to the heat providing unit 1300 based on the corresponding frozen particle size range, the temperature of the refrigerant container RC, the shape of the output end of the composition guide 2100, the adhesive strength between the composition guide 2100 and the composition, and the flow rate of the composition may be selectively determined.

In addition, for a composition that is not appropriate for penetrating into the dermis of the skin, for example, a composition that is not classified as a medicine or drug, the size of frozen particles of the composition may be made small in order to limit the penetration depth to the stratum corneum. For example, the mixing spray system 100 may be designed/controlled so that the size of the frozen particles of the composition is about 10 μm to about 50 μm.

Control of Spray Speed

The penetration effect may be improved as the velocity of frozen particles when the composition reaches the skin surface increases.

As a method of increasing the speed of the frozen particles of the composition, there is a method of reducing the size of the frozen particles. For example, the amount of refrigerant heated before spraying may be increased to reduce the size of the frozen particles. Alternatively, the shape of the end of the composition guide 2100 may be manufactured to be more sharp (pointed).

As a method of increasing the speed of the frozen particles of the composition, there is a method of increasing the spray speed of refrigerant particles that transfer kinetic energy to the composition. For example, the spray speed of the refrigerant particles may be increased by increasing the internal pressure of the refrigerant container RC in which the refrigerant is stored.

In order to increase the speed of the frozen particles of the composition, the length of the above-described acceleration section may be secured at equal to or greater than a predetermined level. In other words, the refrigerant and the composition may be sprayed while the skin surface and the nozzle 1500 are spaced apart from each other by equal to or greater than a minimum acceleration distance. Here, the minimum acceleration distance may be selected within a range of about 3 mm to about 5 mm or about 1 mm to about 10 mm.

The mixing spray system 100 may be designed so that the speed of the frozen particles of the composition is equal to or greater than 50 m/s. Alternatively, the mixing spray system 100 may be designed so that the speed of the frozen particles of the composition is equal to or greater than 60 m/s, 70 m/s, 80 m/s, 90 m/s, 100 m/s, 110 m/s, or 120 m/s. Here, the speed of the frozen particles of the composition may refer to the average moving speed of composition particles moved in the refrigerant spray stream RSS. For example, the speed of the frozen particles of the composition was obtained by tracking each frozen particle in an image captured with the high-speed camera, measuring the moving speed, and calculating the average value. Here, the speed of the frozen particles may be calculated as the average speed of at least parts of particles in the refrigerant spray stream RSS. Alternatively, the speed of the frozen particles may be calculated as the average speed of particles in the above-described observing region OR.

Meanwhile, by increasing the spray speed of the composition, the composition may be prevented from decelerating due to air resistance until it reaches the skin surface. For example, formation of a sheath jet around the refrigerant spray stream RSS may prevent the composition particles from encountering air. To form the sheath jet, the mixing spray system 100 may further include a sheath nozzle. The sheath nozzle may spray the refrigerant or compressed air to surround the refrigerant spray stream RSS. The sheath nozzle is disposed around the nozzle 1500 and may have a ring-shaped spray port. Alternatively, the sheath nozzle may be composed of a plurality of nozzles arranged around the nozzle 1500. When the temperature of the sheath jet is equal to or less than a predetermined level (e.g., the freezing point of the composition), the temperature of the frozen particles of the composition may be prevented from lowering.

Temperature Control for Target Region

In the method of spraying the refrigerant and the composition together, the temperature or pressure of the refrigerant, the temperature of the skin surface due to the refrigerant, etc. may significantly affect the penetration ability of the composition into the skin. For example, as described above, the temperature or pressure of the refrigerant may contribute to causing the composition to be frozen and collide with the skin in a solid state.

Meanwhile, regardless of whether the composition is frozen, the temperature of the skin surface may affect the penetration ability of the composition. For example, when the temperature of the skin surface decreases, the stratum corneum of the skin epidermis becomes hard, so the collision time when the composition collides may be shortened and the impact force of the composition may be increased accordingly, making it easier for the composition to penetrate. Meanwhile, as described above, when the temperature of the skin surface excessively decreases, an ice film may be formed on the skin surface or an ice layer may be formed inside the skin, making it difficult for the composition to penetrate.

Accordingly, the present applicant conducted an experiment to confirm how the penetration effect of the composition varies depending on the temperature of the skin surface.

Method of Controlling Temperature of Skin Surface

The temperature of the skin surface onto which the refrigerant and the composition are sprayed may be controlled by the above-described mixing spray system 100. For example, when the refrigerant and the composition are sprayed onto the skin surface by the mixing spray system 100, the controller 1900 may acquire the real-time temperature of the skin surface measured in real time from the sensor unit 1600, acquire power to be applied to the heat providing unit 1300 using a PID control method that uses the difference between the preset target temperature and the real-time temperature as an input value and the power to be applied to the heat providing unit 1300 as an output value, and heat the refrigerant before spraying by applying the acquired power to the heat providing unit 1300 to maintain the temperature of the skin surface at the target temperature.

The temperature of the skin surface may be maintained at, for example, −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C. Here, maintaining the temperature of the skin surface at a specific temperature means that the temperature measured on the skin surface is within an error range (e.g., −1° C. to +1° C.) at the specific temperature for a predetermined period of time.

Experiment to Determine Degree of Penetration Depending on Temperature of Skin Surface Hereinafter, an experiment to observe the penetration ability of the composition depending on the temperature of the skin surface will be described with reference to FIG. 18, and an appropriate skin surface temperature will be described with reference to experimental data.

The experimental process is as follows.

Rabbits were used as experimental animals. After general anesthesia, the back skin of the rabbits was shaved and divided into 10 areas (3 cm*3 cm). A composition and a refrigerant were sprayed using the mixing spray system 100 according to the first embodiment.

As the composition, FITC-dextran (3 kDA to 5 kDA) in which FITC, i.e., a fluorescent labeling substance was attached to dextran was used.

Thereafter, tissue samples were collected and stained with DAPI, and the fluorescence intensity in the tissue samples was measured using a fluorescence microscope.

Experimental subjects included an untreated group and first to third experimental groups. For the untreated group, FITC-dextran was applied to the rabbit skin surface. For the first experimental group, FITC-dextran was sprayed on the rabbit skin surface while maintaining its temperature at −3° C. For the second experimental group, FITC-dextran was sprayed on the rabbit skin surface while maintaining its temperature at 0° C. For the third experimental group, FITC-dextran was sprayed on the rabbit skin surface while maintaining its temperature at 3° C.

Figure 18:
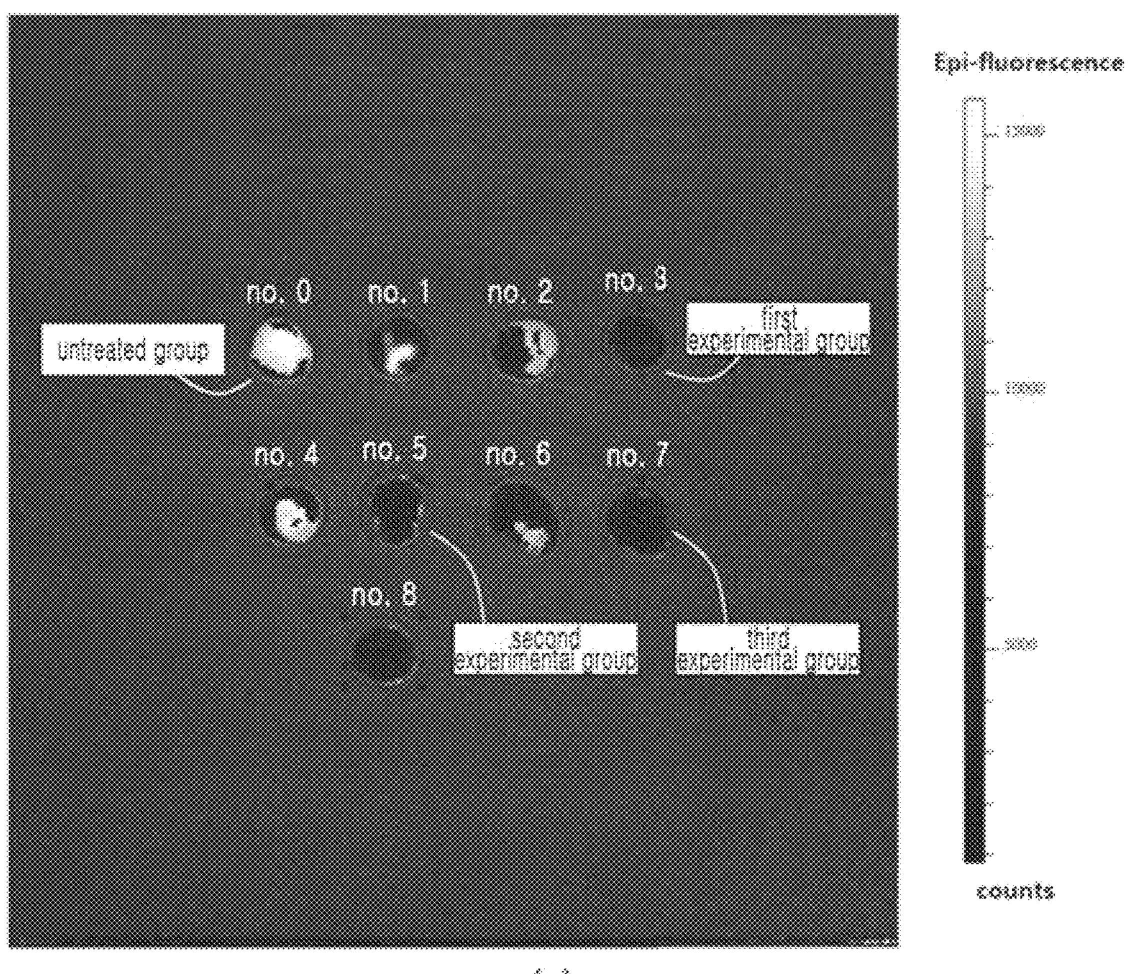
FIG. 18 is a view illustrating the results of an experiment to confirm the penetration effect depending on the temperature of the skin surface.

FIG. 18 is a view illustrating the results of the experiment to confirm the penetration effect depending on the temperature of the skin surface. (a) of FIG. 18 illustrates the fluorescence intensity for each experimental group, and (b) of FIG. 18 illustrates the penetration ability for each experimental group.

Referring to FIG. 18, the penetration ability was higher when the refrigerant and the composition were mixed and sprayed than when the composition was applied. In addition, in the process of spraying the refrigerant and the composition, the penetration ability was highest when the temperature of the skin surface was maintained at 3° C., and the penetration ability was higher when maintained at −3° C. than when the temperature was maintained at 0° C.

As a result, it can be understood that the penetration ability is greatly improved when spraying the refrigerant and the composition while maintaining the temperature of the skin surface at about 3° C.

As can be seen from the above experiment, it was found that the penetration effect of the composition improved when the skin surface temperature was maintained at a specific temperature. Therefore, as described later, it is necessary to determine the penetration ability of the composition while controlling the target temperature of the skin surface and to find the target temperature at which the penetration ability of the composition exceeds a predetermined level.

Method of Determining Target Temperature

Hereinafter, a prophetic example for determining a target temperature at which the skin surface temperature needs to be maintained will be described.

A third experiment is conducted as follows.

The mixing spray system 100 is prepared. Here, as described above, the mixing spray system 100 includes the refrigerant spray device 1000 generating a refrigerant spray stream RSS, and the composition supply device 2000 coupled thereto and enabling a composition to be introduced into the refrigerant spray stream RSS. The internal pressure of the refrigerant container RC where a refrigerant is stored is 50 bar, and carbon dioxide is used as the refrigerant.

The refrigerant spray device 1000 of the mixing spray system 100 includes a thermoelectric element for applying heat to the refrigerant and adopts a PID control method that provides power to the thermoelectric element based on the real-time temperature obtained by measuring the temperature of the target region.

Rabbits are used as experimental animals. After general anesthesia, the back skin of the rabbits is shaved and divided into 10 areas (3 cm*3 cm). The composition and the refrigerant are sprayed using the mixing spray system 100. Here, the target temperature of the rabbit skin surface is set to 0° C.

As the composition, FITC-dextran (3 kDA to 5 kDA) in which FITC, i.e., a fluorescent labeling substance is attached to dextran is used.

After spraying of the composition and the refrigerant, tissue samples are collected and stained with DAPI, and the fluorescence intensity in the tissues samples is measured using a fluorescence microscope.

The target temperature of the skin surface is changed to −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., and 25° C., and the fluorescence intensity (penetration amount) in the tissue samples at each target temperature is measured.

A threshold temperature range when the fluorescence intensity is equal to or greater than a predetermined level is found.

When implementing the mixing spray system 100 in the future, the target temperature may be set within the threshold temperature range.

A fourth experiment is conducted as follows.

The mixing spray system 100 is prepared. Here, as described above, the mixing spray system 100 includes the refrigerant spray device 1000 generating a refrigerant spray stream RSS, and the composition supply device 2000 coupled thereto and enabling a composition to be introduced into the refrigerant spray stream RSS. The internal pressure of the refrigerant container RC where a refrigerant is stored is 50 bar, and carbon dioxide is used as the refrigerant.

The refrigerant spray device 1000 of the mixing spray system 100 includes a thermoelectric element for applying heat to the refrigerant. The refrigerant spray device 1000 is controlled by applying a constant voltage (e.g., 1 V) to the thermoelectric element in the process of spraying the refrigerant.

Rabbits are used as experimental animals. After general anesthesia, the back skin of the rabbits is shaved and divided into 10 areas (3 cm*3 cm). The composition and the refrigerant are sprayed using the mixing spray system 100.

As the composition, FITC-dextran (3 kDA to 5 kDA) in which FITC, i.e., a fluorescent labeling substance is attached to dextran is used.

After spraying of the composition and the refrigerant, tissue samples are collected and stained with DAPI, and the fluorescence intensity in the tissues samples is measured using a fluorescence microscope.

The voltage applied to the thermoelectric element is changed from 0 V to 5 V in 0.1 V increments, and the fluorescence intensity at each applied voltage is measured.

A threshold voltage range when the fluorescence intensity is equal to or greater than a predetermined level is found.

When implementing the mixing spray system 100 in the future, the voltage applied to the thermoelectric element is set within the threshold voltage range.

The features, structures, effects, etc. described in the embodiments are included in at least one embodiment of the present disclosure and are not necessarily limited to one embodiment. Furthermore, the features, structures, effects, etc. provided in each embodiment can be combined or modified in other embodiments by those skilled in the art to which the embodiments belong. Therefore, the contents related to the combination and modification should be construed to be included in the scope of the present disclosure.

The embodiments described herein have been provided merely for illustrative purposes, those skilled in the art will appreciate that various modifications, additions, and substitutions are possible, without departing from the scope and spirit of the present disclosure. In other words, each element specifically shown in the embodiments can be implemented in modified forms. Therefore, the contents related to the combination and modification should be construed to be included in the scope of the present disclosure as disclosed in the accompanying claims.

What is claimed is:

1. A spraying system to spray a composition and a coolant to a skin, the spraying system comprising:

a composition storage configured to store the composition;

a coolant storage spaced apart from the composition storage and configured to store the coolant at a first temperature;

a nozzle configured to continuously spray the coolant toward a target area of the skin via a discharge port thereof such that the continuously sprayed coolant forms a coolant stream having a second temperature;

a valve configured to transport the coolant from the coolant storage to the nozzle;

a composition guide structure configured to guide the composition from the composition storage into the coolant stream such that the composition meets and moves within the coolant stream at a region outside the nozzle, the composition guide structure comprising a body, an input end and an output end disposed on opposing sides of the body, wherein the body, the input end, and the output end are integrally formed as a single guide structure defining the composition guide structure, the body being disposed offset from a central axis of the nozzle, the input end configured as an inlet for introducing the composition from the composition storage into the composition guide structure, the body configured to guide the composition from the input end to the output end within the composition guide structure, the output end configured as an outlet for discharging the composition into the coolant stream, and the output end being positioned outside the nozzle and adjacent to the discharge port of the nozzle such that the composition discharged from the output end meets the coolant stream at the region outside the nozzle, the composition having a third temperature after being discharged from the output end and before being mixed with the coolant stream, the third temperature being higher than the second temperature;

an actuator operatively coupled with the composition storage and the composition guide structure, the actuator configured to pressurize the composition in the composition storage so that the composition is released from the composition storage, introduced into the input end of the composition guide structure, flows along the body of the composition guide structure, and is discharged from the output end of the composition guide structure into the coolant stream outside the nozzle;

a temperature regulator configured to regulate a temperature of the coolant by heating the coolant before the coolant is transported into the nozzle and before the coolant stream meets the composition such that the temperature of the coolant at the temperature regulator increases from the first temperature to a fourth temperature higher than the first temperature; and a controller configured to:

control the temperature regulator to maintain the temperature of the target area at a target temperature sufficient to:

cause at least part of the composition to convert into a plurality of frozen composition particles by mixing the coolant stream having the second temperature with the composition having the third temperature while moving in the coolant stream at the region outside the nozzle, at least some of the plurality of frozen composition particles having a size sufficient to collide with and penetrate into the target area of the skin, and prevent formation of an ice layer on the target area of the skin that would at least partially block penetration of the plurality of frozen composition particles, wherein the temperature regulator is configured to heat the coolant before the coolant reaches the nozzle to maintain the target temperature at or above 0 degrees Celsius or 3 degrees Celsius, so as to increase the temperature of the coolant stream and reduce a number of the plurality of frozen composition particles at the region outside the nozzle, while ensuring both particle penetration and prevention of ice layer formation, as compared to a condition in which the coolant is not heated before reaching the nozzle, such that an amount of the composition penetrating into the target area of the skin is increased due to prevention of formation of the ice layer.

2. The spraying system of claim 1, wherein the controller is configured to:

control the temperature regulator to regulate the temperature of the coolant enabling the coolant to cause at least 2%, at least 5% or at least 17% of the at least part of the composition being converted into the plurality of frozen composition particles within a predetermined observation region, and wherein each of the plurality of frozen composition particles is not in a gaseous state.

3. The spraying system of claim 2, wherein the predetermined observation region is configured at a predetermined distance from the target area.

4. The spraying system of claim 1, wherein the temperature of the coolant stream is configured to be regulated to be insufficient to form the ice layer due to a temperature of the target area which is higher than the temperature of the coolant stream while the temperature of the coolant stream still causes the at least some of the composition to be converted into the plurality of frozen composition particles.

5. The spraying system of claim 1, further comprising:

a distance maintaining part configured to maintain a distance between the nozzle and the target area.

6. The spraying system of claim 1, wherein the output end of the composition guide structure is spaced apart from the discharge port of the nozzle by a first distance in a direction parallel to a central axis of the nozzle and by a second distance in a direction orthogonal to the central axis of the nozzle.

7. The spraying system of claim 1, wherein the composition guide structure comprises a composition guide plate.

8. The spraying system of claim 1, wherein the controller is further configured to control the temperature regulator to regulate the temperature of the target area to cause a freeze ratio of the composition to be in a range of 2% and 74% and prevent ice layer formation on the target area of the skin by maintaining the target temperature at or above 0 degrees Celsius or 3 degrees Celsius.

9. A method of penetrating a composition into a skin of a subject using a spraying system, the method comprising:

providing the spraying system, wherein the spraying system comprises a composition storage configured to store the composition, a composition guide structure, an actuator, a nozzle, a valve, a temperature regulator, a coolant storage configured to store a coolant at a first temperature, a coolant storage connector coupled to the coolant storage and a spraying hole through which a coolant stream sprayed from the nozzle is sprayed together with the composition, the coolant stream having a second temperature, the composition guide structure configured to guide the composition from the composition storage into the coolant stream such that the composition meets and moves within the coolant stream at a region outside the nozzle, the composition guide structure comprising a body, an input end and an output end disposed on opposing sides of the body, wherein the body, the input end, and the output end are integrally formed as a single guide structure defining the composition guide structure, the body being disposed offset from a central axis of the nozzle, the composition having a third temperature after being discharged from the output end and before being mixed with the coolant stream, the third temperature being higher than the second temperature, the actuator operatively coupled with the composition storage and the composition guide structure, the actuator configured to pressurize the composition in the composition storage so that the composition is released from the composition storage, introduced into the input end of the composition guide structure, flows along the body of the composition guide structure, and is discharged from the output end of the composition guide structure into the coolant stream outside the nozzle;

positioning the spraying hole of the spraying system to face a target area which is a part of the skin; and operating the spraying system to:

regulate a temperature of the coolant, being transported into the nozzle, by heating the coolant before the coolant meeting the composition, such that the temperature of the coolant at the temperature regulator increases from the first temperature to a fourth temperature higher than the first temperature, to maintain the temperature of the target area at a target temperature to:

cause at least part of the composition to convert into a plurality of frozen composition particles by mixing the coolant stream having the second temperature with the composition having the third temperature while moving in the coolant stream at the region outside the nozzle, at least some of the plurality of frozen composition particles having a size sufficient to collide with and penetrate into the target area of the skin, and prevent formation of an ice layer on the target area of the skin that would at least partially block penetration of the plurality of frozen composition particles; and spray the coolant stream to meet the composition at the region outside the nozzle and to be delivered toward the target region together with the composition, wherein the temperature regulator is configured to heat the coolant before the coolant reaches the nozzle to maintain the target temperature at or above 0 degrees Celsius or 3 degrees Celsius, so as to increase the temperature of the coolant stream and reduce a number of the plurality of frozen composition particles at the region outside the nozzle, while ensuring both particle penetration and prevention of ice layer formation, as compared to a condition in which the coolant is not heated before reaching the nozzle, such that an amount of the composition penetrating into the target area of the skin is increased due to prevention of formation of the ice layer.

10. The method of claim 9, wherein operating the spraying system comprises:

operating the spraying system to regulate the coolant passing through the temperature regulator such that the coolant to be sprayed from the nozzle causes at least 2%, at least 5% or at least 17% of the composition mixed with the coolant stream converted into the plurality of frozen composition particles within a predetermined observation region, and wherein each of the plurality of frozen composition particles is not in a gaseous state.

11. The method of claim 10, wherein the predetermined observation region is configured at a predetermined distance from the target area.

12. The method of claim 9, wherein the temperature of the coolant stream to be sprayed from the nozzle is regulated to be insufficient to form the ice layer due to a temperature of the target area which is higher than the temperature of the sprayed coolant while the temperature of the coolant stream still causes the at least part of the composition to be converted into the plurality of frozen composition particles.

13. The method of claim 9, wherein the spraying system further comprises a distance maintain part, and wherein positioning the spraying hole of the spraying system comprises:

positioning the spraying hole of the spraying system at a distance between the spraying hole and the target area to be maintained by the distance maintain part.

* * * * *